US008914103B2

United States Patent
Kim et al.

(10) Patent No.: US 8,914,103 B2
(45) Date of Patent: Dec. 16, 2014

(54) DEVICE AND IONTOPHORESIS PATCH COMPRISING THIN FILM BATTERY

(75) Inventors: Nam-In Kim, Gwangju-si (KR); Myoung-Woo Chung, Gwangju-si (KR); Seung-Gyu Lim, Gwangju-si (KR); Kwang-Suk Kim, Gwangju-si (KR)

(73) Assignee: Rocket Electric Co., Ltd, Gwangju-Si (KR)

( * ) Notice: Subject to any disclaimer, the term of this patent is extended or adjusted under 35 U.S.C. 154(b) by 222 days.

(21) Appl. No.: 13/503,586

(22) PCT Filed: Oct. 21, 2010

(86) PCT No.: PCT/KR2010/007251
§ 371 (c)(1),
(2), (4) Date: Apr. 23, 2012

(87) PCT Pub. No.: WO2011/049391
PCT Pub. Date: Apr. 28, 2011

(65) Prior Publication Data
US 2012/0226219 A1    Sep. 6, 2012

(30) Foreign Application Priority Data
Oct. 22, 2009 (KR) .......... 10-2009-0100831

(51) Int. Cl.
*A61N 1/30* (2006.01)
*H01M 6/18* (2006.01)
*H01M 6/40* (2006.01)
*H01M 10/04* (2006.01)
*A61N 1/32* (2006.01)
*A61N 1/04* (2006.01)

(52) U.S. Cl.
CPC ............. *A61N 1/0428* (2013.01); *A61N 1/325* (2013.01); *A61N 1/0448* (2013.01); *H01M 2300/0082* (2013.01); *H01M 6/181* (2013.01); *A61N 1/303* (2013.01); *H01M 6/40* (2013.01); *H01M 10/0436* (2013.01)
USPC ........................................ 604/20

(58) Field of Classification Search
USPC ...................... 604/20; 424/447, 449
See application file for complete search history.

(56) References Cited

U.S. PATENT DOCUMENTS

2002/0188241 A1*  12/2002  Morris et al. .............. 604/20
2010/0228180 A1*  9/2010  Jayes et al. ................ 604/20

FOREIGN PATENT DOCUMENTS

| JP | 09-056827 A | 3/1997 |
|---|---|---|
| JP | 2000-067908 A | 3/2000 |

(Continued)

OTHER PUBLICATIONS

International Search Report of International Application No. PCT/KR2010/007251, dated Aug. 1, 2011.

*Primary Examiner* — Theodore Stigell
*Assistant Examiner* — Benjamin Koo
(74) *Attorney, Agent, or Firm* — Revolution IP, PLLC

(57) ABSTRACT

An apparatus having a thin film battery includes: a device electrically operating and including a substrate; and the thin film battery for supplying power to the device. The thin film battery includes: a first electrically conductive layer formed on the substrate; a second electrically conductive layer formed on the substrate while being spaced apart from the first electrically conductive layer and positioned on an identical plane to the first electrically conductive layer; a first electrode layer formed on the first electrically conductive layer and electrically connected to the first electrically conductive layer; a second electrode layer formed on the second electrically conductive layer, electrically connected to the second electrically conductive layer, disposed while being spaced apart from the first electrode layer in a side direction, and having a polarity opposite to a polarity of the first electrode layer; an ion conductive polymer electrolyte for covering both the first electrode layer and the second electrode layer; and a sealing film for sealing the ion conductive polymer electrolyte.

16 Claims, 21 Drawing Sheets

(56) References Cited

FOREIGN PATENT DOCUMENTS

| | | |
|---|---|---|
| JP | 2009-034117 A | 2/2009 |
| KR | 10-0760748 B1 | 9/2007 |
| KR | 10-0816554 B1 | 3/2008 |
| KR | 10-0868350 B1 | 11/2008 |
| KR | 10-2009-0106926 A | 10/2009 |
| WO | WO 2008/114918 A1 | 9/2008 |
| WO | WO 2009/125960 A2 | 10/2009 |

* cited by examiner

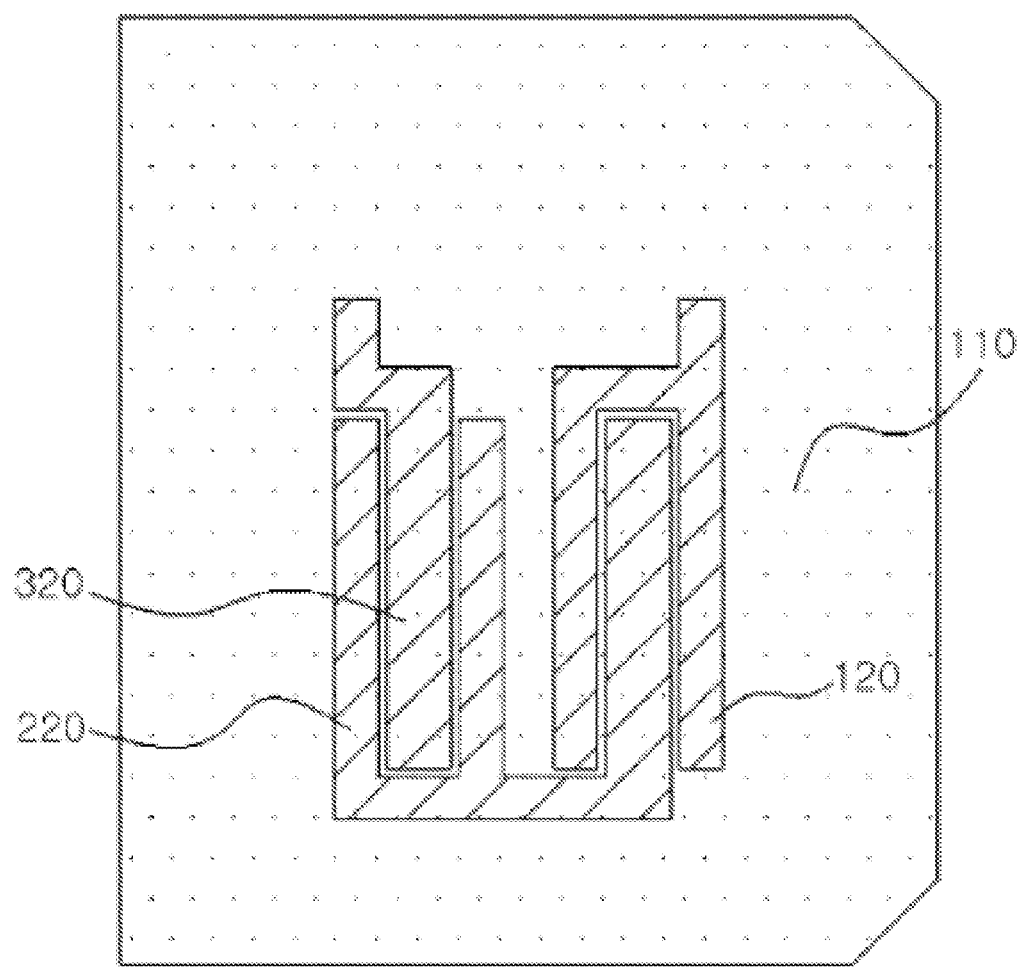

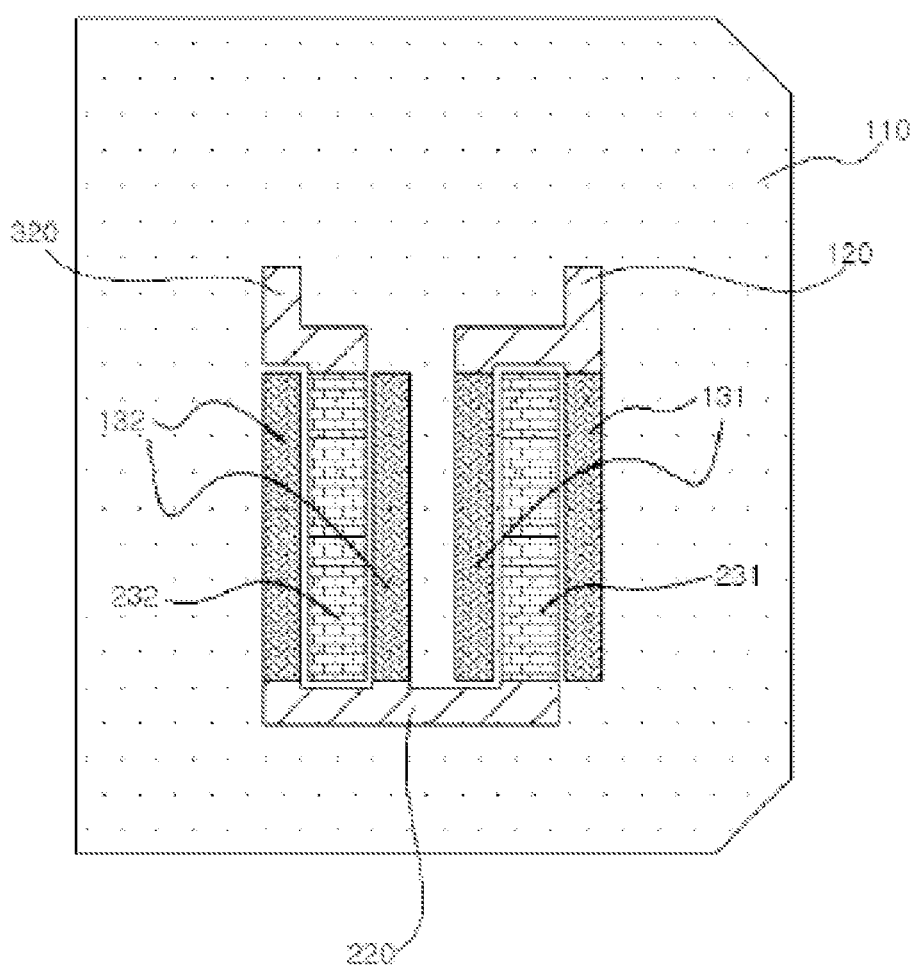

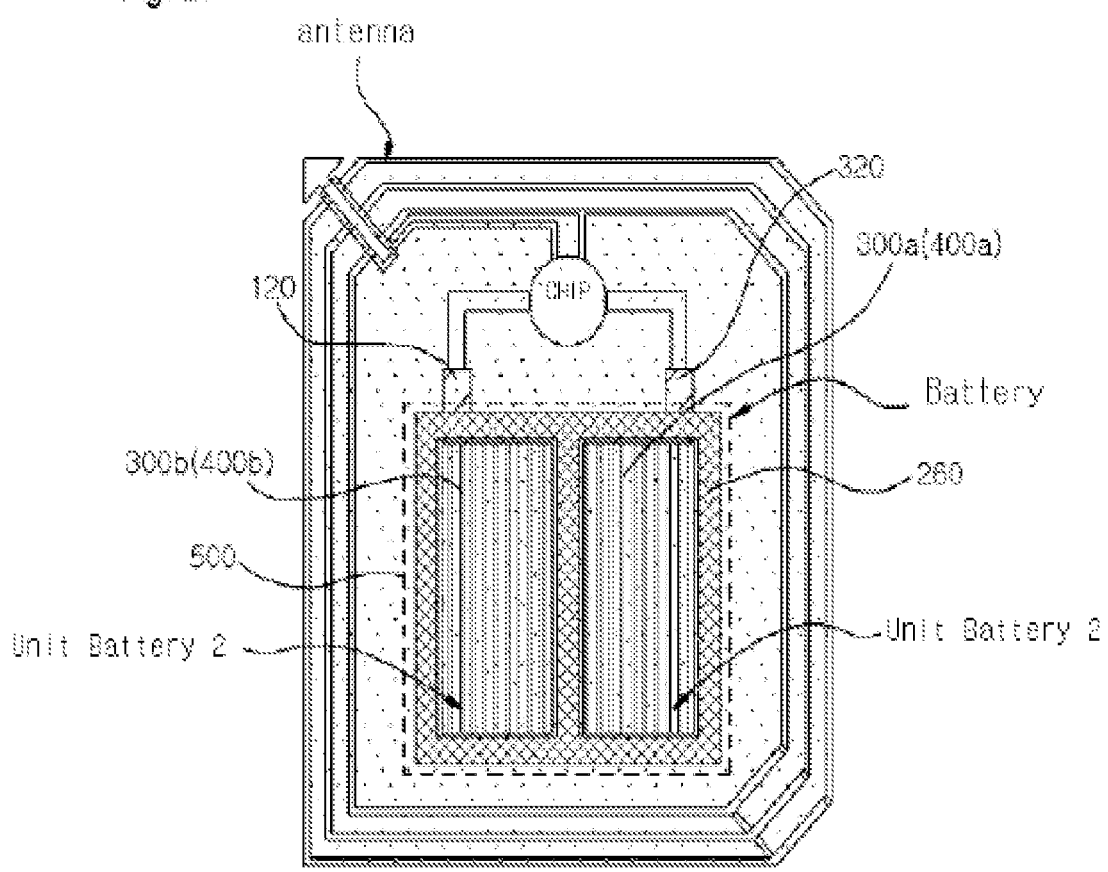

DEVICE AND IONTOPHORESIS PATCH COMPRISING THIN FILM BATTERY

TECHNICAL FIELD

The present invention relates to an apparatus including an iontophoresis patch equipped with a thin film battery, and more particularly, the apparatus having a battery and a device integrally connected to the battery which improves current density and has an advantage to make the apparatus thin and improve manufacturing productivity.

BACKGROUND ART

Iontophoresis refers to a technique for making a micro current flow into the skin and making a material of interest having charges pass into the skin through electrical repulsive force. An iontophoresis patch is used for passing a material of interest, such as a medicine or a cosmetic material, through the skin by using electrical repulsive force. When a patch coated with a material of interest is attached to the skin, a circuit is formed and a current flows, and the material of interest passes into the skin by the electrical repulsive force. It is known that a speed of passing the material of interest is directly affected by a quantity of current flowing into the skin.

A conventional iontophoresis patch is manufactured by a method of independently manufacturing a thin film battery and a patch or a pad including electrically conductive electrodes and then electrically connecting and assembling the electrically conductive electrodes with the thin film battery. The iontophoresis patch manufactured by the aforementioned method has problems of the increase of the current resistance due to a complex current flow route, and low productivity and high manufacturing costs resulting from a complex assembling procedure.

The battery mounted on the iontophoresis patch functions as an energy resource for generating a current, and generally includes two electrodes serving as a positive electrode and a negative electrode and an ion conductive electrolyte. In general, manganese dioxide is used as a material of the positive electrode and zinc is used as a material of the negative electrode, and a gel-type electrolyte, in which zinc chloride or ammonium chloride is dissolved in water together with polymers, is induced into the battery. When binders within the electrodes are dissolved in an aqueous electrolyte during the distribution of the battery after the manufacturing, it results in a short together with the increase of the resistance, thereby sharply deteriorating the performance of the battery. Especially, when it fails to secure the durability of the electrodes against the aqueous electrolyte in a case when the positive electrode is located adjacent to the negative electrode without an isolation film therebetween, a conductive material within the electrodes is separated, so that it serves as a current crosslink with respect to an opposite electrode and thus the short phenomenon is easily generated. In order to overcome the drawback, the electrode, especially the negative electrode, has inevitably employed zinc shaped like a foil or a strip as the material of the electrode. However, if the metal foil is employed as an electrode active material, a reaction area is decreased compared to the electrode manufactured in a powder state, so that a high power property is weak and the productivity is easily decreased.

In order to solve the problems, especially low productivity and the high electrical resistance, Patent Application No. 2007-99132 entitled "Iontophoresis patch and Method of Manufacturing the same" previously filed by the applicant of the present invention discloses the construction in which a patch and a battery are configured as one system by directly coating a material of electrodes on a conductive layer within the patch, which was conceived so as to reduce a contact resistance against the skin. The patch having the aforementioned construction has a structure advantageous to increase the passing of a material of interest into the skin according to a simple current mechanism and a small resistance. However, the patch has a problem in that a material of interest having a weak electrochemical tolerance involves the battery reaction. Further, it is necessary to further simplify a patch manufacturing process and further secure a flexibility of the patch.

As noted from the above description, a lower productivity, high manufacturing costs, a performance deterioration resulting from the electrode structure destruction during the distribution, etc. are now obstacles to the commercialization of the iontophoresis patch. Accordingly, a technical approach is necessary in order to effectively solve the aforementioned problems of the existing iontophoresis patch.

An electric and electronic device consuming a micro current, as well as the iontophoresis patch, may use a thin film battery as a power resource. For example, the thin film battery may be used for devices including a Radio Frequency Identification (RFID) tag, a smart card, and an electronic paper display. In the device having the thin film battery, it is necessary to further decrease manufacturing costs through the reduction of the number of manufacturing processes, further improve the flexibility of the device, and stably supply a power to the thin film battery.

DETAILED DESCRIPTION OF THE INVENTION

Technical Problem

Accordingly, the present invention has been made to solve the above-mentioned problems occurring in the prior art, and the present invention provides an apparatus equipped with a thin film battery, which has a high manufacturing productivity and a strong durability, and is advantageous to secure the flexibility according to a thin shape. Further, the present invention provides an iontophoresis patch equipped with a thin film battery which has a high manufacturing productivity and a strong durability, and is advantageous to secure the flexibility according to a thin shape.

Technical Solution

In accordance with an aspect of the present invention, there is provided an apparatus including a thin film battery, the apparatus including: a device electrically operating and including a substrate; and the thin film battery for supplying power to the device, wherein the thin film battery includes: a first electrically conductive layer formed on the substrate; a second electrically conductive layer formed on the substrate while being spaced apart from the first electrically conductive layer and positioned on an identical plane to the first electrically conductive layer; a first electrode layer formed on the first electrically conductive layer and electrically connected to the first electrically conductive layer; a second electrode layer formed on the second electrically conductive layer, electrically connected to the second electrically conductive layer, disposed while being spaced apart from the first electrode layer in a side direction, and having a polarity opposite to a polarity of the first electrode layer; an ion conductive polymer electrolyte for covering both the first electrode layer and the second electrode layer; and a sealing film for sealing the ion conductive polymer electrolyte. The first electrode layer and the second electrode layer may be disposed on an identical plane.

According to an embodiment of the present invention, the thin film battery is a closed-type thin film battery, and the substrate and the sealing film have a water blocking property. At least one of the substrate and the sealing film is a polyethylene terephthalate film or a polyacrylonitrile film.

The first electrically conductive layer and the second electrically conductive layer may contain one or more conductive powder selected from the group consisting of carbon powder, nickel powder, and silver powder. The first electrode layer is a positive electrode layer of the thin film battery, and may include a binder containing one or more elements selected from the group consisting of polyethylen oxide, polyvinyl pyrrolidone, and polymethyl methacrylate, and manganese dioxide powder. The second electrode layer is a negative electrode layer of the thin film battery, and may include a binder containing one or more elements selected from the group consisting of polyethylene oxide, polyvinyl pyrrolidone, and polymethyl methacrylate, and zinc powder or zinc alloy powder.

The second electrode layer may include zinc alloy powder to which one or more gas generation inhibiting inhibitors selected from the group consisting of bismuth (Bi), indium (In), and aluminum (Al) are added. At least one of the bismuth (Bi), indium (In), and aluminum (Al) as the inhibitor may be contained in the zinc alloy powder by a content of 10 to 1000 ppm, respectively.

The ion conductive polymer electrolyte may be a gel-type electrolyte to which a polymer material is selected from the group consisting of polyethylene oxide, polyvinyl alcohol, and carbonyl methyl cellulose is added. The ion conductive polymer electrolyte may be provided while being impregnated in a hygroscopic paper.

The thin film battery may further include a double-sided adhesive film disposed between the substrate and the sealing film and coated around the ion conductive polymer electrolyte, wherein the sealing film is attached on the double-sided adhesive film to seal the ion conductive polymer electrolyte.

According to an embodiment of the present invention, the thin film battery may further include two or more serially connected unit batteries disposed on the substrate, wherein the thin film battery further includes: a third electrically conductive layer formed on the substrate while being separated from the first and second electrically conductive layers and positioned on an identical plane to the first electrically conductive layer; a third electrode layer electrically connected with the second electrically conductive layer on the second electrically conductive layer, disposed while being spaced apart from the second electrode layer in a side direction, and having an identical polarity to the polarity of the first electrode layer; a fourth electrode layer electrically connected with the third electrically conductive layer on the third electrically conductive layer, disposed while being spaced apart from the third electrode layer in a side direction, and having an identical polarity to the polarity of the second electrode layer; and an additional ion conductive electrolyte separated from the ion conductive polymer electrolyte while covering both the third electrode layer and the fourth electrode layer. The sealing film may seal the ion conductive polymer electrolyte covering both the first electrode layer and the second electrode layer and the additional ion conductive electrolyte covering both the third electrode layer and the fourth electrode layer.

According to an embodiment of the present invention, the second electrically conductive layer may be disposed between the first electrically conductive layer and the third electrically conductive layer. The second electrode layer may be closely disposed to the first electrode layer so that the first and second electrode layers function as electrodes of a first unit battery, and the fourth electrode layer may be closely disposed to the third electrode layer so that the third and fourth electrode layers function as electrodes of a second unit battery.

The first and second electrode layers and the ion conductive polymer electrolyte covering both the first and second electrode layers form a first unit battery, and the third and fourth electrode layers and the additional ion conductive electrolyte covering both the third and fourth electrode layers form a second unit battery. Further, the first unit battery and the second unit battery are serially connected to each other through the second electrically conductive layer.

The thin film battery may further include a double-sided adhesive film disposed between the substrate and the sealing film to seal two or more unit batteries. The double-sided adhesive film has two or more openings, in which the first and second electrode layers and the ion conductive polymer electrolyte covering both the first and second electrode layers may be disposed on one opening and the third and fourth electrode layers and the additional ion conductive electrolyte covering both the third and fourth electrode layers may be disposed on another opening. The ion conductive polymer electrolyte covering both the first and second electrode layers and the additional ion conductive electrolyte covering both the third and fourth electrode layers may be disposed, while being separated from each other, by the double-sided adhesive film.

According to an embodiment of the present invention, the device may be an active pad for transferring a transcutaneous property of a compound, and the apparatus including the thin film battery may be an iontophoresis patch. According to another embodiment of the present invention, the device may be a Radio Frequency Identification (RFID) tag or a smart card.

In accordance with another aspect of the present invention, there is provided an iontophoresis patch including a thin film battery mounted inside the iontophoresis patch, the iontophoresis patch including: a shape variable substrate; a first electrically conductive layer formed on the substrate; a second electrically conductive layer formed on the substrate while being separated from the first electrically conductive layer and positioned on an identical plane to the first electrically conductive layer; a first electrode layer formed on the first electrically conductive layer and being in contact with a part of the first electrically conductive layer; a second electrode layer formed on the second electrically conductive layer, being in contact with a part of the second electrically conductive layer, disposed while being spaced apart from the first electrode layer in a side direction, and having a polarity opposite to a polarity of the first electrode layer; an ion conductive polymer electrolyte for covering both the first electrode layer and the second electrode layer; and a sealing film for sealing the ion conductive polymer electrolyte. The first electrode layer and the second electrode layer are disposed on an identical plane.

The iontophoresis patch may further include a double-sided adhesive film disposed between the substrate and the sealing film and coated around the ion conductive polymer electrolyte, wherein the sealing film is attached on the double-sided adhesive film to seal the ion conductive polymer electrolyte.

The iontophoresis patch may further include a backing layer attached to a rear surface of the substrate and exposed to an outside of an edge of the substrate, wherein the backing layer includes an adhesive material coated on an attached surface thereof attached to the substrate, so that an adhesive property is provided to a part exposed to the outside of the edge of the substrate such that the iontophoresis patch is attached to a target object.

According to another embodiment of the present invention, the iontophoresis patch may further include: a third electrically conductive layer formed on the substrate while being separated from the first and second electrically conductive layers and positioned on an identical plane to the first electrically conductive layer; a third electrode layer electrically connected with the second electrically conductive layer on the second electrically conductive layer, disposed while being spaced apart from the second electrode layer in a side direction, and having an identical polarity to the polarity of the first electrode layer; a fourth electrode layer electrically connected with the third electrically conductive layer on the third electrically conductive layer, disposed while being spaced apart from the third electrode layer in a side direction, and having an identical polarity to the polarity of the second electrode layer; and an additional ion conductive electrolyte separated from the ion conductive polymer electrolyte while covering both the third and fourth electrode layers. The sealing film may seal the ion conductive polymer electrolyte covering both the first and second electrode layers and the additional ion conductive electrolyte covering both the third and fourth electrode layers.

The first and second electrode layers and the ion conductive polymer electrolyte covering both the first and second electrode layers form a first unit battery, the third and fourth electrode layers and the additional ion conductive electrolyte covering both the third and fourth electrode layers form a second unit battery, and the first unit battery and the second unit battery are serially connected to each other through the second electrically conductive layer.

Effect of the Invention

Accordingly, the present invention improves manufacturing productivity of the apparatus, such as the iontophoresis patch, a smart card, and an RFID tag, including the thin film battery, and the current density according to the shortness of the route of the current flow. Further, the present invention enhances the aging stability of the apparatus, such as the iontophoresis patch, including the thin film battery according to the introduction of the non-aqueous binder. Further, the present invention more easily secures the flexibility of the apparatus, such as the iontophoresis patch, according to the decrease of a thickness of the apparatus.

BRIEF DESCRIPTION OF THE DRAWINGS

FIG. 6 is a plan view illustrating the patch of FIG. 5 including a backing layer attached to a rear surface of the substrate, a front surface of which the electrically conductive layers and the electrode layers are coated on.

FIG. 14 is a plan view illustrating the patch of FIG. 13 including a backing layer attached to a rear surface of the substrate, a front surface of which the electrically conductive layers and the electrode layers are coated on.

FIG. 19 is a plan view illustrating electrically conductive layers formed on a substrate of an RFID tag in an apparatus including a thin film battery according to an embodiment of the present invention.

FIG. 20 is a plan view illustrating first to fourth electrode layers coated on a part of the electrically conductive layers of FIG. 19.

FIG. 21 is a plan view illustrating an RFID tag coupled with a plurality of unit batteries using the electrode layers of FIG. 20.

DESCRIPTION OF REFERENCE NUMBERS FOR MAIN PARTS OF THE DRAWINGS

Figure 1:
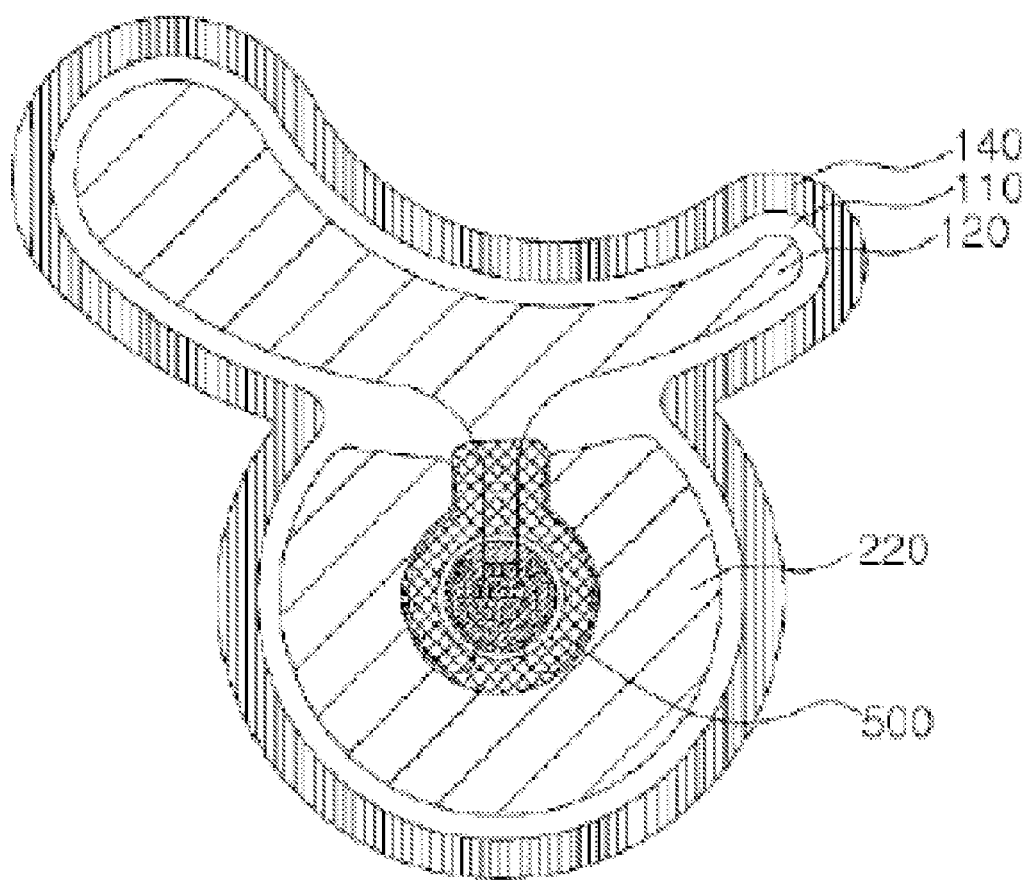
FIG. 1 is a plan view illustrating an iontophoresis patch according to an embodiment of the present invention.

110: Substrate
120: First electrically conductive layer
130, 131: First electrode layer
132: Third electrode layer
140: Backing layer
220: Second electrically conductive layer
230, 231: Second electrode layer
232: Fourth electrode layer
260: Double-sided adhesive film
400, 400a, 400b: Hygroscopic paper
300, 300a, 300b: Ion conductive polymer electrolyte layer
500: Sealing film

BEST MODE FOR CARRYING OUT THE INVENTION

Hereinafter, exemplary embodiments of the present invention will be described with reference to the accompanying drawings. Therefore, the present invention is not limited to the following embodiments but may be implemented in other forms. In the drawings, the shapes, sizes and the like of elements are exaggerated for convenience of illustration. Like reference numerals indicate like elements throughout the specification and drawings.

FIG. 1 is a plan view illustrating an iontophoresis patch according to an embodiment of the present invention. Referring to FIG. 1, the iontophoresis patch includes a substrate 110 having a variable shape, and a first electrically conductive layer 120 and a second electrically conductive layer 220 formed on the substrate 110. The first electrically conductive layer 120 and the second electrically conductive layer 220 are connected to a positive electrode and a negative electrode of a thin film battery system integrally formed with the patch within the patch, respectively, and a material of interest (e.g. cosmetics, medicine, or the like) to be injected to a human body, etc. may be laid on any one of or both the first electrically conductive layer 120 and the second electrically conductive layer 220. The material of interest having a polarity may be passed into the skin by an electrical repulsive force using an electron flow or a current resulting from a battery reaction of the thin film battery formed within the iontophoresis patch.

Further, a backing layer 140 is attached to a surface, i.e. a rear surface of the substrate 110, opposite to a front surface of the substrate 110 on which the first and second electrically conductive layers 120 and 220 are disposed. An adhesive material of an attachment surface of the backing layer 140 is exposed along an edge of the substrate 110. Through the exposed adhesive material of the backing layer 140, the iontophoresis patch may be easily attached to the skin, etc.

A more detailed construction of the iontophoresis patch of FIG. 1 is illustrated in FIGS. 2 to 10. The iontophoresis patch of FIG. 1 may be manufactured in an order from FIGS. 2 to 10. Hereinafter, the iontophoresis patch according to the embodiment of the present invention will be described in detail with reference to FIGS. 2 to 10.

Figure 2:
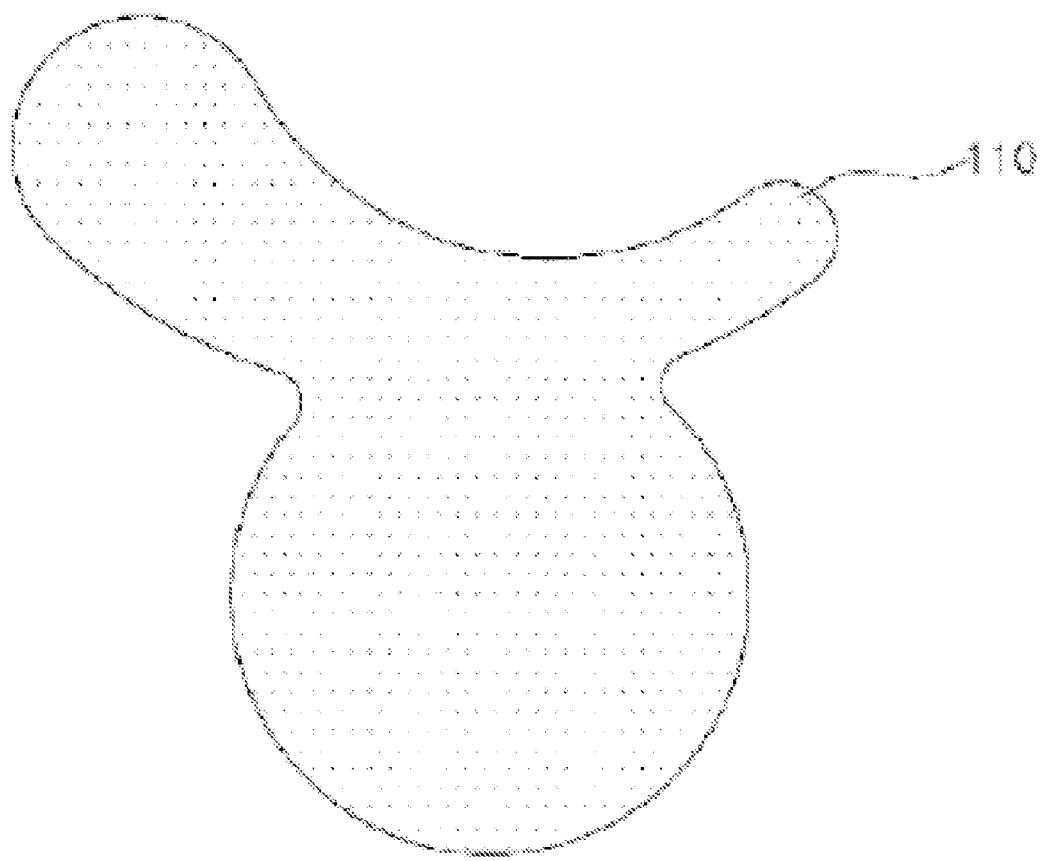
FIG. 2 is a plan view illustrating a substrate of the iontophoresis patch of FIG. 1.

The substrate 110 for the iontophoresis patch shaped like a flat surface illustrated in FIG. 2 may be used in the present invention. However, the present invention is not limited to the aforementioned shape of the flat surface, and may use any design of the substrate shaped like the flat surface for the iontophoresis patch. The substrate 110 may be made of various materials, such as polymer or a soluble plastic substrate, which are bendable (or shape-variable) according to a shape of a target object (e.g. skin of a person) having the flexibility and curves. For example, the substrate 110 is several tens or hundreds of microns in thickness, and may be made of a polyacrylonitrile film, a polyethylene terephthalate film, a polyimide film, etc., and an appropriate material for the substrate 110 may be selected considering the moisture permeability, the film flexibility, etc.

Figure 3:
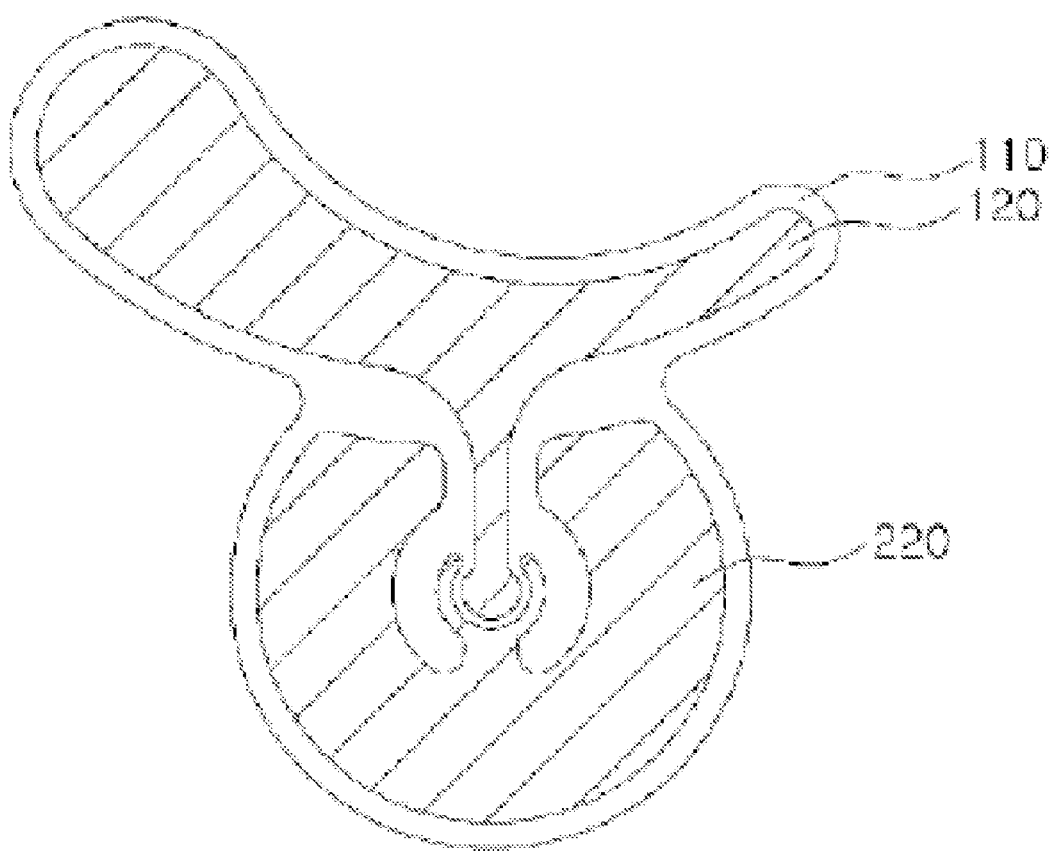
FIG. 3 is a plan view illustrating a first electrically conductive layer and a second electrically conductive layer coated on the substrate of FIG. 2.

As illustrated in FIG. 3, the first electrically conductive layer 120 and the second electrically conducive layer 220 having different polarities are disposed in the front surface of the substrate 110. The first electrically conductive layer 120 and the second electrically conducive layer 220 are disposed on the same plane on the substrate 110 while being separated from each other. The battery electrodes and the electrolyte are disposed at a region in which the first electrically conductive layer 120 is adjacent to the second electrically conducive layer 220 as described to be later, so that the thin film battery is formed. In the present embodiment, the first electrically conductive layer 120 is shaped like a "T" and the second electrically conductive layer 220 has a shape of surrounding a center portion indicated with slash lines of the T-shaped first electrically conductive layer 120. However, the present invention is not limited to such shapes of the electrically conductive layers.

The first electrically conductive layer 120 and the second electrically conducive layer 220 may be manufactured by, for example, coating a carbon ink consisting of carbon powder and binders on the substrate 110 by approximately 15 μm, followed by drying the carbon ink at approximately 60° C. for two hours. The carbon ink may be directly prepared by mixing the appropriate binders, a solvent, and micron carbon powder, or a complete product-type commercialized carbon ink may be used. Conductive powder including silver powder, copper powder, and nickel powder, or a mixture thereof may be used instead of the carbon powder. A viscosity of the carbon ink shows approximately 36,000 to 50,000 cps, but the viscosity may be controlled considering a coating processibility.

Figure 4:
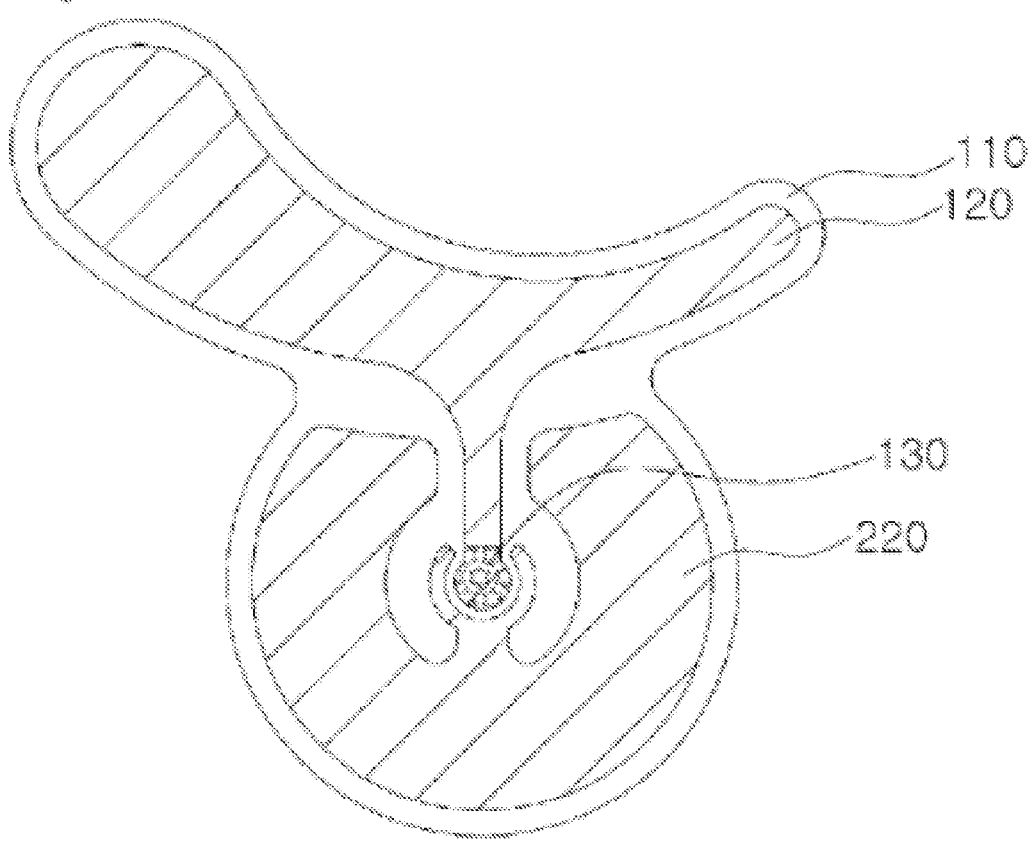
FIG. 4 is a plan view illustrating a first electrode layer coated on a part of the first electrically conductive layer of FIG. 3.

Referring to FIG. 4, a first electrode layer 130 is coated on a portion adjacent to the second electrically conductive layer 220 as a part of the first electrically conductive layer 120. The first electrode layer 130 is in contact with the part of the first electrically conductive layer 120 (and thus the first electrode layer 130 is electrically connected to the first electrically conductive layer 120), and serves as one electrode (one of the positive electrode and the negative electrode) of the thin film battery as described later.

Figure 5:
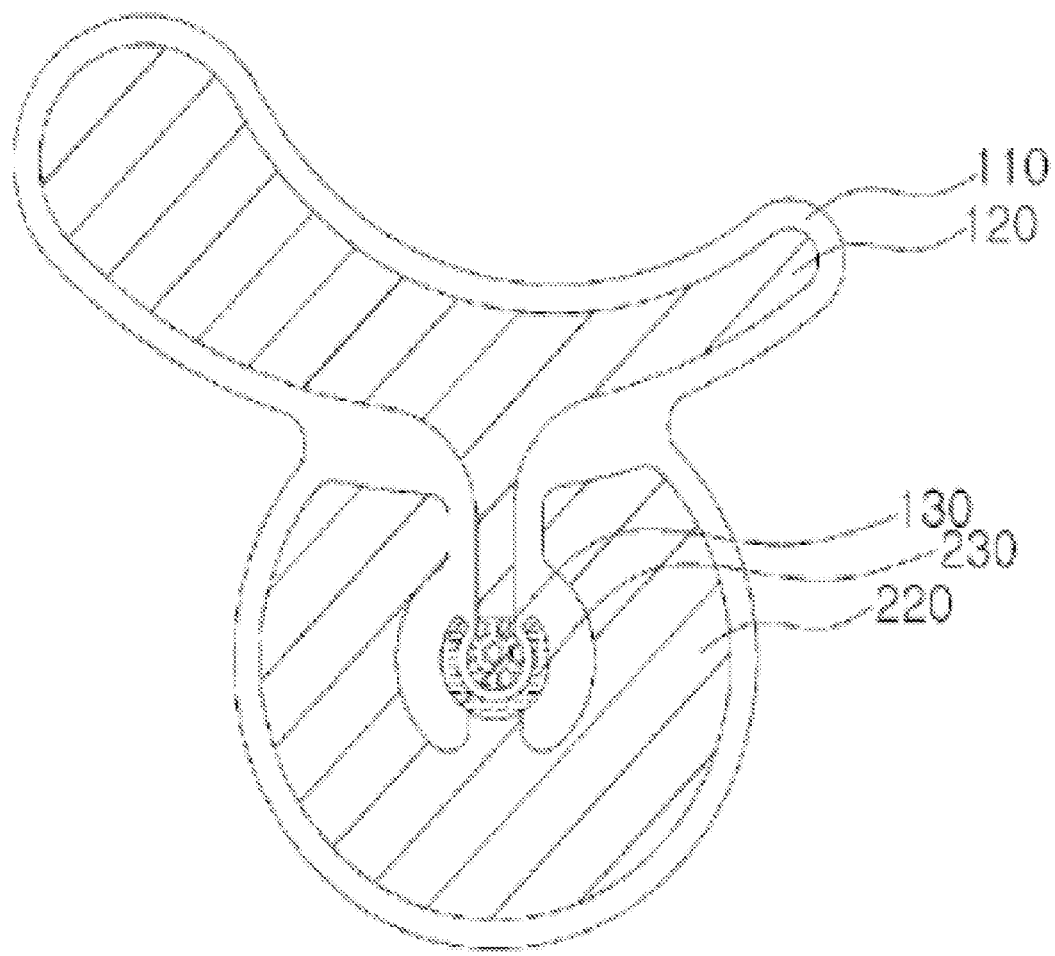
FIG. 5 is a plan view illustrating a second electrode layer coated on a part of the second electrically conductive layer of FIG. 4.

Referring to FIG. 5, a second electrode layer 230 is coated on a portion adjacent to the first electrically conductive layer 120 as a part of the second electrically conductive layer 220. The second electrode layer 230 is in contact with the part of the second electrically conductive layer 220 (and thus the second electrode layer 230 is electrically connected to the second electrically conductive layer 220), and serves as the other electrode (one having a polarity opposite to that of the first electrode layer 130 between the positive electrode and the negative electrode) of the thin film battery as described later. Especially, as illustrated in FIG. 5, the first electrode layer 130 and the second electrode layer 230 are disposed while being spaced apart from each other in a side direction. Further, the first electrode layer 130 and the second electrode layer 230 may be substantially disposed on the same plane.

The first electrode layer 130 may be used as the positive electrode of the thin film battery. In this case, the first electrode layer 130 that is the positive electrode may be manufactured by mixing manganese dioxide powder, a conductive material, and a binder solution and making a mixture in a slurry state, and then coating the mixture on the first electrically conductive layer 120, followed by drying the mixture. A process of preparing the slurry includes the steps of dry-mixing manganese dioxide in a powder state having a grain size of approximately 40 μm or less and carbon black and adding a mixture to the binder solution, followed by stirring. Various materials may be considered as a material of the positive electrode generating electricity, but the manganese dioxide is preferable for the material of the electrode considering an electric capacity, a voltage, an electrochemical property, a distribution environment of a product, etc. Multi-component binders including a mixture of aqueous binders and non-aqueous binders may be applied to the manufacturing of the electrode. Polyethylene oxide and polyvinyl pyrrolidone are generally appropriate for the aqueous binders, and polymethyl methacrylate is appropriate for the non-aqueous binders. When the aqueous binders are mixed with the non-aqueous binders in the manufacturing of the electrode, it is effective to enhance the durability of the electrode.

The second electrode layer 230 may be used as the negative electrode of the thin film battery. In this case, in order to manufacture the second electrode layer 230 that is the negative electrode, a slurry for manufacturing the second electrode layer is prepared by dry-mixing zinc powder having a grain size of approximately 45 µm or less and carbon black that is a conductive material and adding a mixture to an already prepared binder solution.

For the zinc powder used as the negative electrode active material, pure zinc powder or alloy type zinc power may be used. For the purpose of inhibiting gas release generated during the storage or the discharge in the battery, the alloy type zinc powder (zinc alloy powder) may use a type in which aluminum (AL), bismuth (Bi), indium (In), or the like, are added to the zinc. Likewise to the positive electrode, a multicomponent binder system, such as polyethylene oxide, polyvinyl pyrrolidone, and polymethyl methacrylate, may be applied to the negative electrode. In the manufacturing of the electrode, the multi-component binder system including the mixture of two or more types of binders is advantageous in the aspects of the electrical efficiency, a mechanical strength, and an adhesive force with the electrically conductive layer, compared to a single binder. Especially, the introduction of polymethyl methacrylate to the aqueous binder, such as polyethylene oxide and polyvinyl pyrrolidone, effectively improves the durability of the electrode and the manufacturing processibility. The second electrode layer 230 is manufactured by coating electrode slurry on the second electrically conductive layer 220 by using a coating device and drying the electrode slurry in a drying furnace set to 60° C. for two or more hours.

In general, when the electrode layer is dissolved in the electrolyte, the electrode structure is destroyed, the resistance increases, and conductive particles within the electrode, are separated, so that a short phenomenon is occurred to have the separated conductive particles being electrically connected to the adjacent electrode. Especially, such a short phenomenon is accelerated in the electrode using only the aqueous binders as the binders. In order to prevent the generation of the short phenomenon, a metal foil or strip has been conventionally used as the negative electrode, but it is weak to obtain a momentary peak current due to the decrease of the reaction area, compared to the electrode employing the powder. Accordingly, in order to sufficiently exert the reaction performance of the battery, it is important to select the binders forming the electrode. In this respect, when the multi-component binder system in which the non-aqueous binders are mixed with the aqueous binders is induced, the durability of the electrode may be maintained and the electrode resistance may be stabilized.

The manganese dioxide and the zinc in the powder state respectively used in the manufacturing of the first electrode layer 130 serving as the positive electrode and the second electrode layer 230 serving as the negative electrode are effective to achieve the high current density and improve the electrode manufacturing processibility. As illustrated in FIGS. 4 and 5, according to the shapes of the first and second electrode layers 130 and 230, the second electrode layer 230 surrounds the edge of the first electrode layer 130 and is adjacent to the first electrode layer 130, so that the resistance generated during the generation of the current may be minimized.

Figure 6:
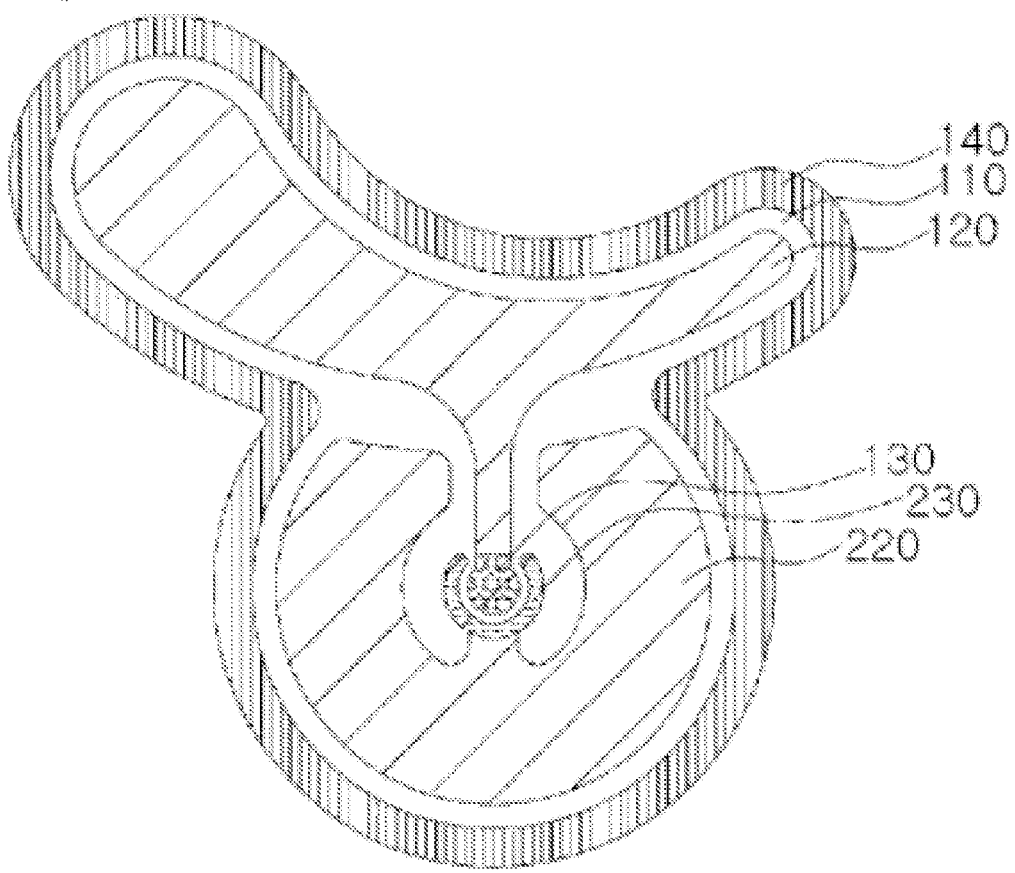

Next, referring to FIG. 6, the backing layer 140 is attached to the surface, i.e. the rear surface of the substrate 110, opposite to the front surface (on which the first and second electrically conductive layers 120 and 220 are coated) of the substrate 110. The backing layer 140 may be nonwoven fabric with an adhesive material coated on an attachment surface thereof. Polyurethane or rayon of artificial fiber may be appropriately used as a main material of the backing layer 140. A color of a surface opposite to the attachment surface of the backing layer 140 may be determined according to visual preference, and a necessary phrase may be printed or designed as a matter of convenience.

As illustrated in FIG. 6, the backing layer 140 is formed to have a larger size than that of the substrate 110 in such a manner that the adhesive material of the backing layer 140 is exposed along the edge of the substrate 110 (see a portion indicated with vertical lines). As described above, the adhesive material of the backing layer 140 exposed to the edge of the substrate 110 provides the adhesive property or increases the attachment force when the iontophoresis patch is attached to the skin, or the like, of a person.

Figure 7:
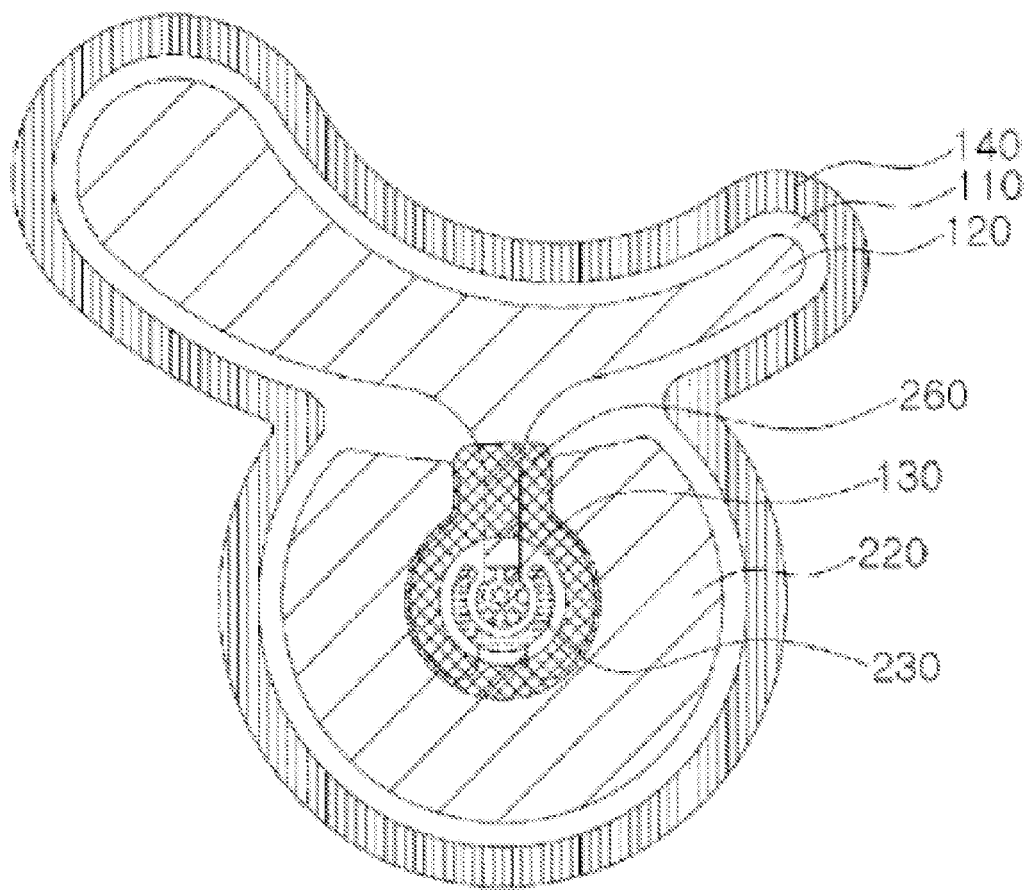
FIG. 7 is a plan view illustrating the patch of FIG. 6 to which a double-sided adhesive film for sealing a battery system is attached.

Next, referring to FIG. 7, a double-sided adhesive film 260 enclosing the outside of the first and second electrode layers 130 and 140 is partially coated (including the attachment of the double-sided adhesive film) on the substrate 110 and the electrically conductive layers. The double-sided adhesive film 260 may be provided for sealing of the battery system so as to prevent the electrolyte loss of the thin film battery together with a sealing film (see reference number 500 of FIG. 10) attached to the double-sided adhesive film 260 as described later. However, the double-sided adhesive film is not essentially necessary for the sealing of the battery system, and for example, the battery may be sealed by a method of welding the sealing film to the substrate by heat.

Figure 8:
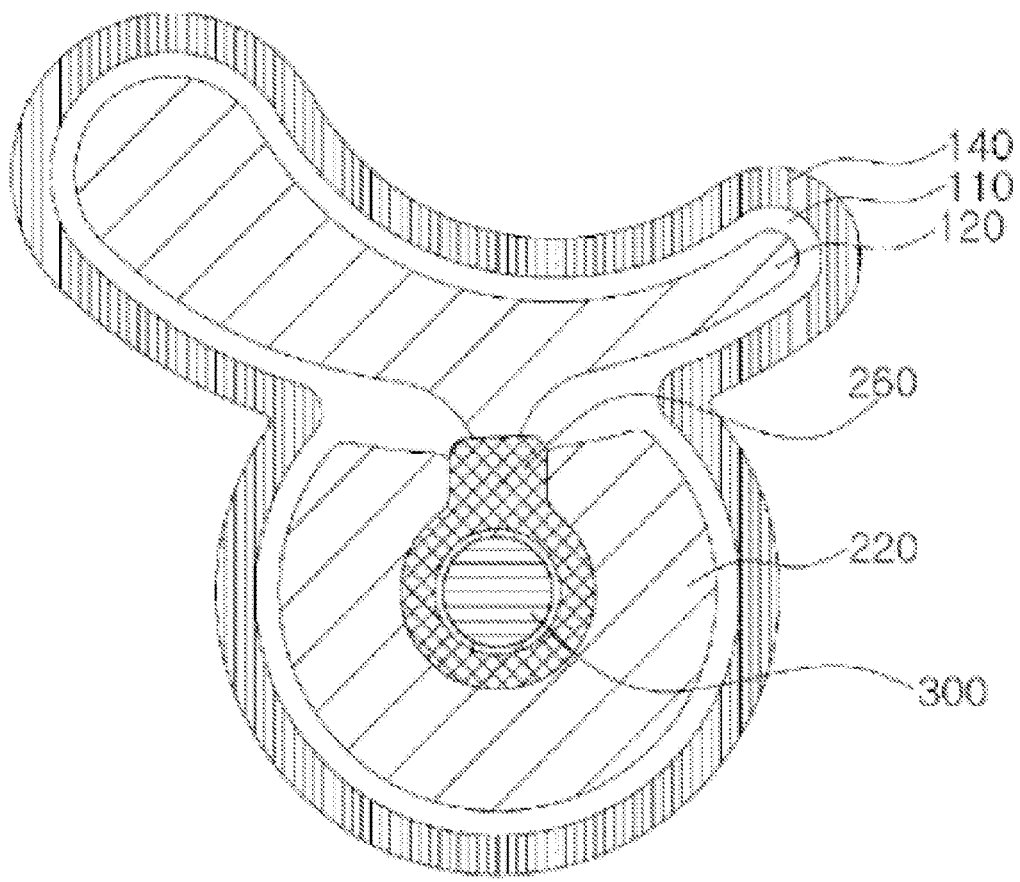
FIG. 8 is a plan view illustrating the patch of FIG. 7 in which an ion conductive electrolyte is coated on the regions of electrode layers.
Figure 9:
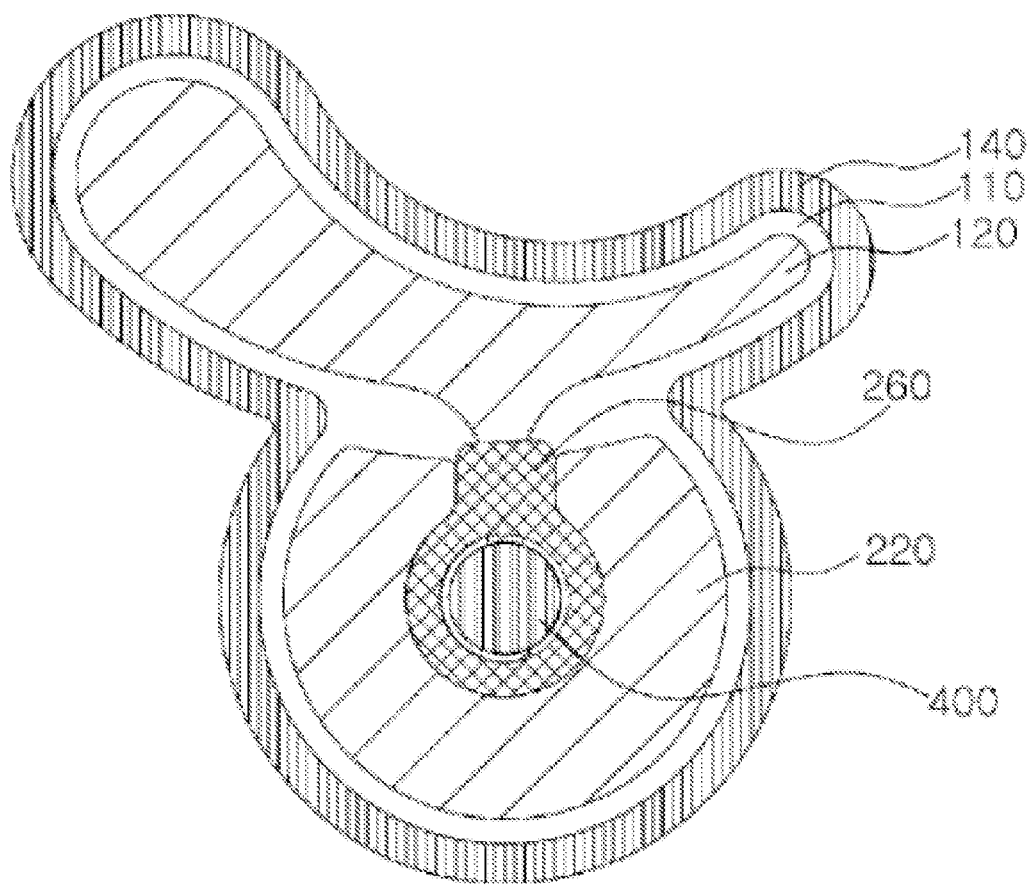
FIG. 9 is a plan view illustrating the patch of FIG. 7 in which a hygroscopic paper impregnated with an ion conductive electrolyte is disposed.

Next, referring to FIG. 8, an ion conductive polymer electrolyte layer 300 for covering both the first electrode layer 130 and the second electrode layer 230 is formed on the substrate 110. The ion conductive polymer electrolyte layer 300 is disclosed in the inside of the double-sided adhesive film 260, so that the double-sided adhesive film 260 encloses the edge of the ion conductive polymer electrolyte layer 300. Alternatively, as illustrated in FIG. 9, a hygroscopic paper 400 impregnated with an ion conductive polymer electrolyte is disposed such that the hygroscopic paper 400 covers both the first and second electrode layers 130 and 230. In this case, the hygroscopic paper 400 containing the electrolyte is disposed in the inside of the double-sided adhesive film 260 so that the double-sided adhesive film 260 encloses an edge of the hygroscopic paper 400. The first and second electrically conductive layers 120 and 220, the first and second electrode layers 130 and 230, and the electrolyte layer 300 disposed therebetween correspond to the basic elements of the thin film battery according to the embodiment of the present invention.

In order to prepare the ion conductive polymer electrolyte, an aqueous electrolyte in which zinc chloride ($ZnCl_2$) or ammonium chloride ($NH_4Cl$) is mixed with purified water, is used. When the electrolyte, in which zinc chloride ($ZnCl_2$) or ammonium chloride ($NH_4Cl$) is mixed, is introduced, the high current performance and the intermittent discharge performance may be advantageously achieved at the same time. Since the evaporation of the electrolyte causes the rapid performance deterioration of the battery, the dropping of a vapor pressure of the electrolyte by melting polymer in the electrolyte is induced in order to control the performance deterioration of the battery. Polyethylene oxide, polyvinyl alcohol, carbonyl methyl cellulose, etc. may be used as the polymer.

The hygroscopic paper 400 impregnated with the ion conductive electrolyte functions to absorb the electrolyte and regularly supply electrolytic elements necessary in the electrodes during the battery reaction. However, the electrolyte layer may be directly used without the use of the hygroscopic paper 400 as described above (see FIG. 8). Paper or nonwoven fabric having a high hygroscopic property may be used as the hygroscopic paper 400, and the thickness of the hygroscopic paper 400 is appropriately 30 to 200 µm.

Figure 10:
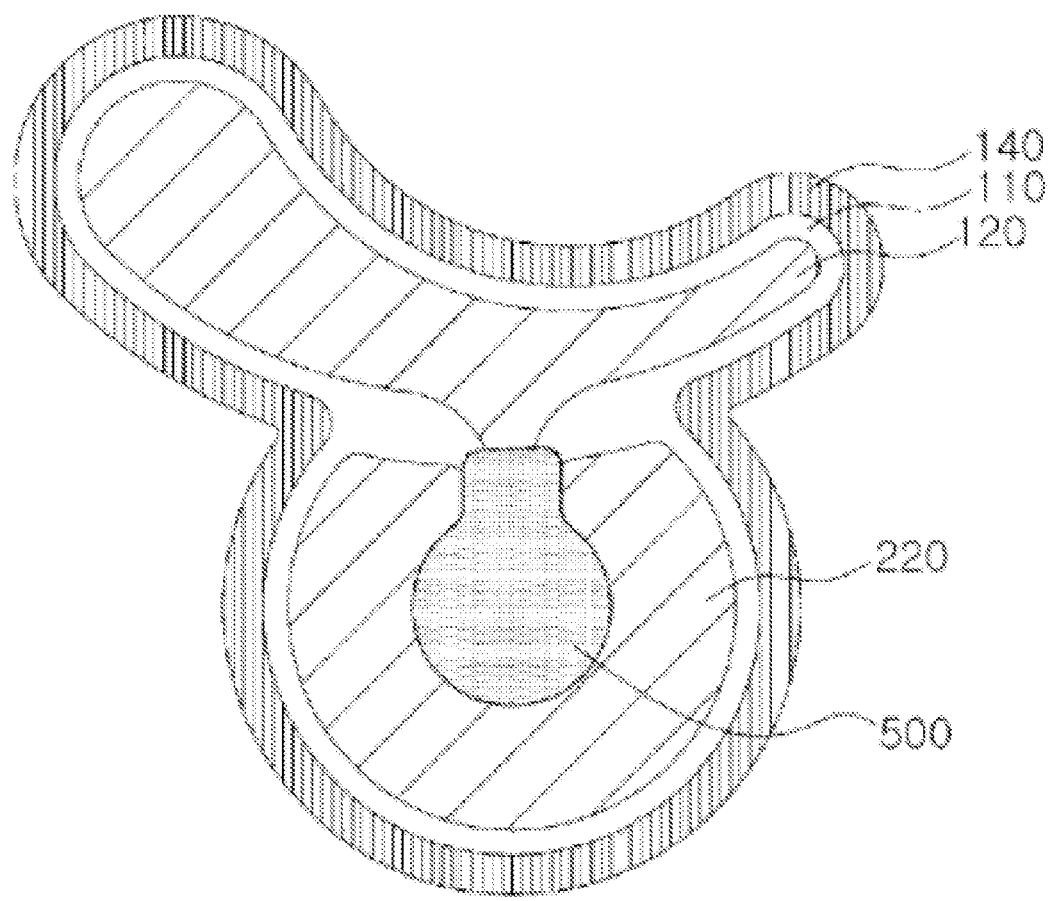
FIG. 10 is a plan view illustrating the patch of FIG. 8 or 9 to which a sealing film for sealing a battery system is attached.

Next, referring to FIG. 10, a sealing film 500 is disposed in order to block the electrolyte from evaporating to the outside by sealing the battery system including the first and second electrode layers 130 and 230 and the electrolyte region 300 or 400. The sealing film 500 is attached on the aforementioned double-sided adhesive film (see reference number 260 of FIG. 8 or 9), to seal the ion conductive polymer electrolyte layer (or the hygroscopic paper impregnated with the electrolyte). The sealing film may be made of polyacrylonitrile, polyethylene terephthalate, polyimide, or the like, and may use the film made of the same material as the substrate 110. As described above, the battery system may be sealed by applying heat to the substrate 110 and welding the sealing film 500 on the substrate 110 without the double-sided adhesive film 260, instead of the attachment of the sealing film 500 to the double-sided adhesive film 260.

The battery system is sealed using the substrate 110, the double-sided adhesive film 260, and the sealing film 500. In this case, the water depletion of the electrolyte within the battery system may be effectively controlled by making the substrate 110, the double-sided adhesive film 260, and the sealing film 500 of a material have a water blocking property. Accordingly, the thin film battery integrally formed with the iontophoresis patch may be a closed-type battery. A gas release issue (e.g. swelling, layer separation, performance deterioration within the sealed battery due to the release of gas, such as hydrogen, released from the negative electrode) in the closed-type battery may be solved by using the zinc alloy powder, to which an inhibitor, such as Al, Bi, and In, is added, as the material of the negative electrode (e.g. the second electrode layer). At least one of Al, Bi, and In as the inhibitor added to the negative electrode active material may be contained in the zinc alloy powder with the content of 10 to 1000 ppm.

In FIG. 10, the material of interest (cosmetic or medicine to be injected into the skin) is laid on a part of the electrically conductive layer 120 or 220 exposed to the outside. When the material of interest to be injected into the skin of the person takes on the negative charge, the material of interest is laid on the electrically conductive layer (e.g. the second electrically conductive layer) connected to the negative electrode (e.g. the second electrode layer) of the battery, and when the material of interest to be injected into the skin of the person takes on the positive charge, the material of interest is laid on the electrically conductive layer (e.g. the first electrically conductive layer) connected to the positive electrode (e.g. the first electrode layer) of the battery. Accordingly, the electrical repulsive force is generated using the iontophoresis patch so that the material of interest passes into the skin.

According to the aforementioned embodiment, the battery electrodes are directly formed and the electrolyte is coated on the electrically conductive layers on the single substrate without a separated current collector, so that manufacturing productivity of the iontophoresis patch is improved and the current density is improved due to the shortening of the route of the current flow. According to the introduction of the non-aqueous binders, the aging stability of the apparatus, such as the iontophoresis patch, including the thin film battery is improved. Further, the positive electrode and the negative electrode are not laminated up and down while having the electrolyte therebetween, but the positive electrode and the negative electrode (the first and second electrode layers) are spaced apart from each other in a side direction and the electrolyte covers the positive electrode and the negative electrode, so that the thickness of the apparatus is decreased, thereby more easily securing the flexibility of the apparatus.

According to another embodiment of the present invention, the aforementioned embodiment is basically used and the iontophoresis patch including two or more serial-connected batteries may be provided. In such a patch, a plurality of electrically conductive layers and a plurality of electrode layers may be formed within the single patch. An example of a construction of the iontophoresis patch in which two or more unit batteries are serially connected is illustrated in FIGS. 11 to 18. The iontophoresis patch illustrated in FIG. 18 may be manufactured in order from FIGS. 11 to 18. Hereinafter, referring to FIGS. 11 to 18, the iontophoresis patch including a plurality of serial-connected unit batteries will be described in detail.

Figure 11:
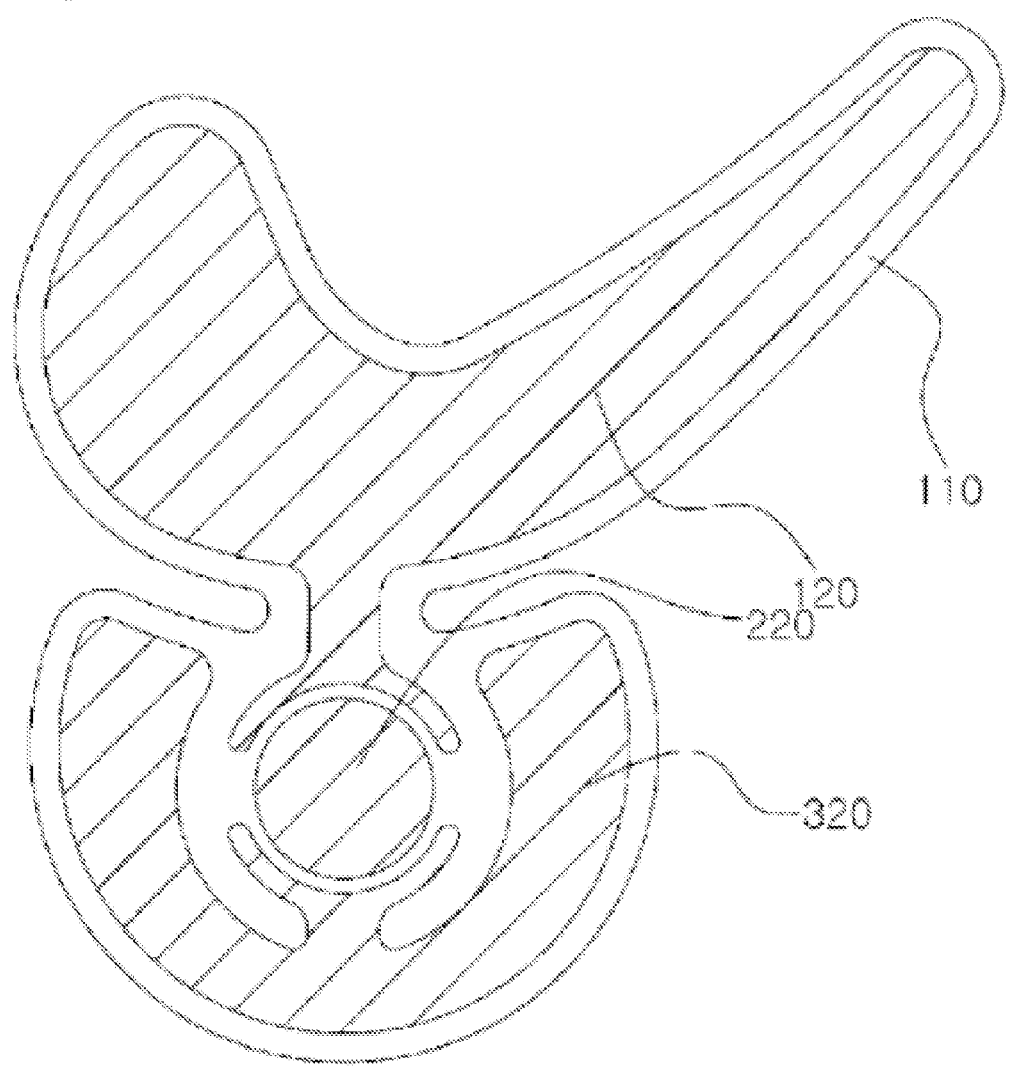
FIG. 11 is a plan view illustrating first to third electrically conductive layers coated on a substrate in an iontophoresis patch in which two unit batteries are serially connected according to an embodiment of the present invention.

Referring to FIG. 11, the first electrically conductive layer 120, the second electrically conductive layer 220, and a third electrically conductive layer 320 are disposed on the substrate 110. The first to third electrically conductive layers 120, 220, and 320 are disposed on the same plane while being spaced apart from each other. In the present embodiment, the second electrically conductive layer 220 is disposed between the first electrically conductive layer 120 and the third electrically conductive layer 320, but the present invention is not limited to such a disposition structure or shape.

Figure 12:
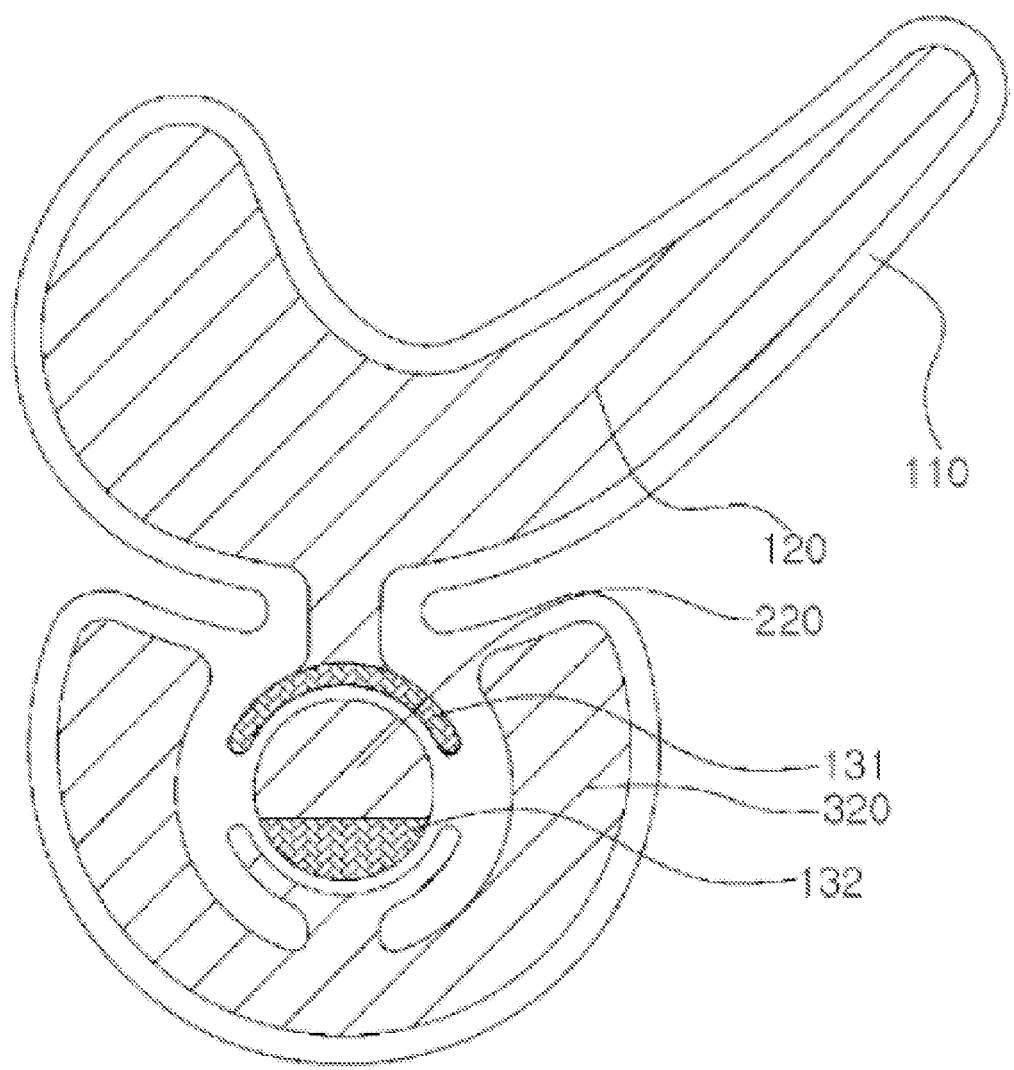
FIG. 12 is a plan view illustrating a first electrode layer and a third electrode layer coated on a part of the electrically conductive layer of FIG. 11.
Figure 13:
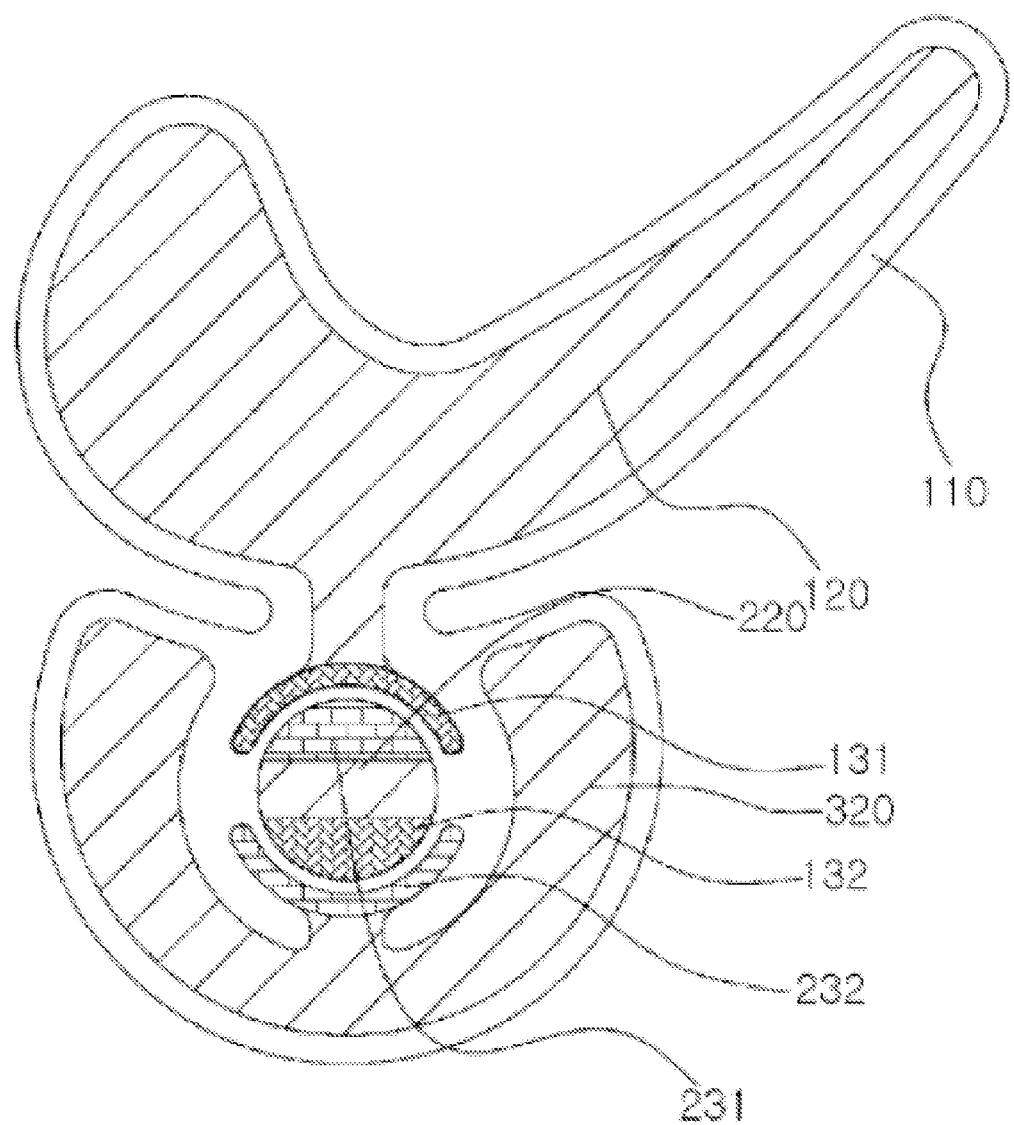
FIG. 13 is a plan view illustrating a second electrode layer and a fourth electrode layer coated on a part of the electrically conductive layer of FIG. 12.

Referring to FIG. 12, a first electrode layer 131 contacting the first electrically conductive layer 120 is coated on a part of the first electrically conductive layer 120, and a third electrode layer 132 contacting the second electrically conductive layer 220 is coated on a part of the second electrically conductive layer 220. Further, referring to FIG. 13, a second electrode layer 231 contacting the second electrically conductive layer 220 is coated on a part of the second electrically conductive layer 220, and a fourth electrode layer 232 contacting the third electrically conductive layer 320 is coated on a part of the third electrically conductive layer 320. Especially, the first to fourth electrode layers 131, 231, 132, and 232 are spaced apart from each other in a side direction. Especially, the second electrode layer 231 and the third electrode layer 132 are disposed on the same plane of the second electrically conductive layer 220, but are positioned in different regions and spaced apart from each other in the side direction. The first electrode layer 131 and the second electrode layer 231 are adjacent to each other and the third electrode layer 132 and the fourth electrode layer 232 are adjacent to each other.

The first electrode layer 131 and the second electrode layer 231 have different polarities (e.g. if the first electrode layer 131 is a positive electrode, the second electrode layer 231 is a negative electrode). Further, the third electrode layer 132 and the fourth electrode layer 232 have different polarities (e.g. if the third electrode layer 132 is a positive electrode, the fourth electrode layer 232 is a negative electrode). Further, the first electrode layer 131 and the third electrode layer 132 have the same polarity (e.g. the positive electrode), and the second electrode layer 231 and the fourth electrode layer 232 have the same polarity (e.g. the negative electrode). A material and a manufacturing process of the electrode layers according to each polarity may employ the material and the manufacturing process described in the aforementioned embodiment.

The adjacently disposed first electrode layer 131 and second electrode layer 231 become the positive electrode and the negative electrode of one unit battery (a first unit battery), respectively, and the adjacently disposed third electrode layer 132 and fourth electrode layer 232 become the positive electrode and the negative electrode of the other unit battery (a second unit battery), respectively, which will be described later. Further, the first unit battery and the second unit battery are serially connected to each other through the second electrically conductive layer 220 because both the second electrode layer 231 (e.g. the negative electrode) of the first unit battery and the third electrode layer 132 (e.g. the positive electrode) of the second unit battery are disposed while being in contact with the second electrically conductive layer 220.

Figure 14:
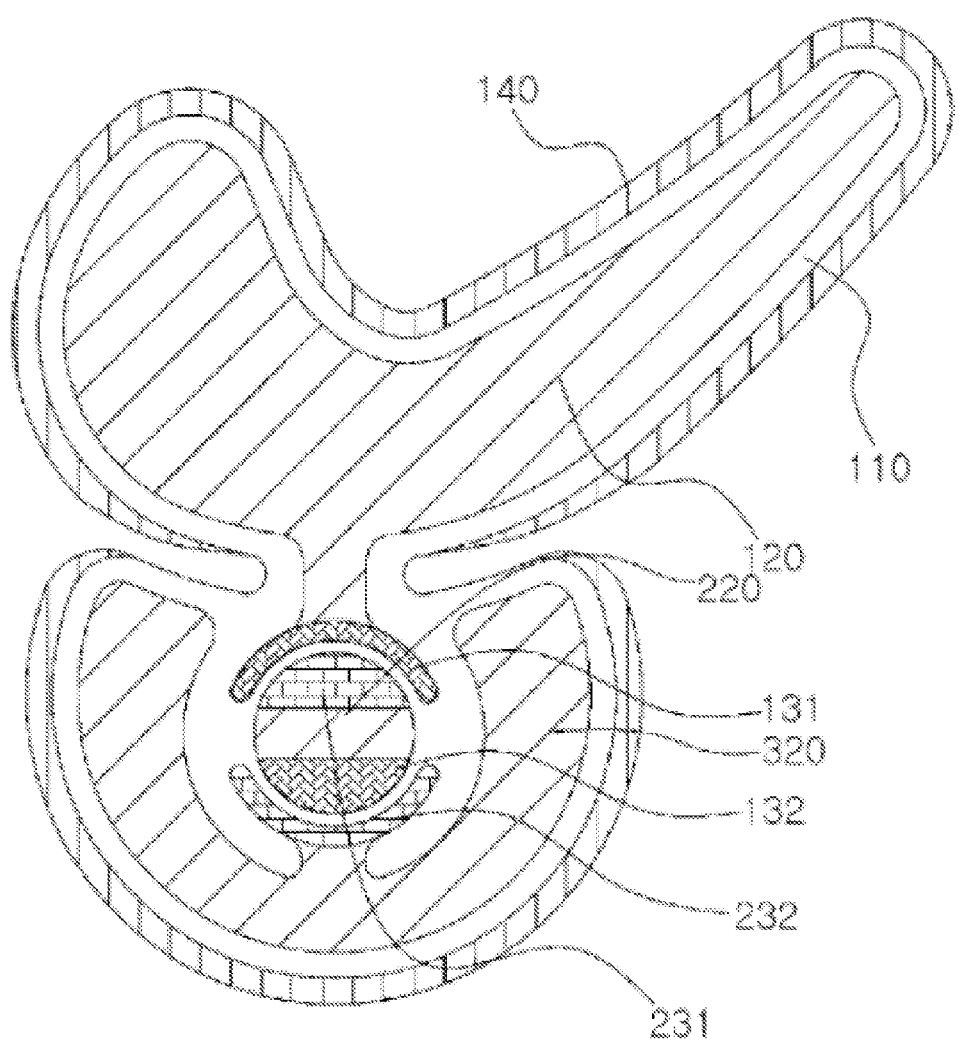

Next, referring to FIG. 14, the backing layer 140 is attached to the rear surface of the substrate 110. Likewise to the aforementioned embodiment, the patch may be easily attached to the skin, etc., through an adhesive layer of the exposed region of the backing layer 140.

Figure 15:
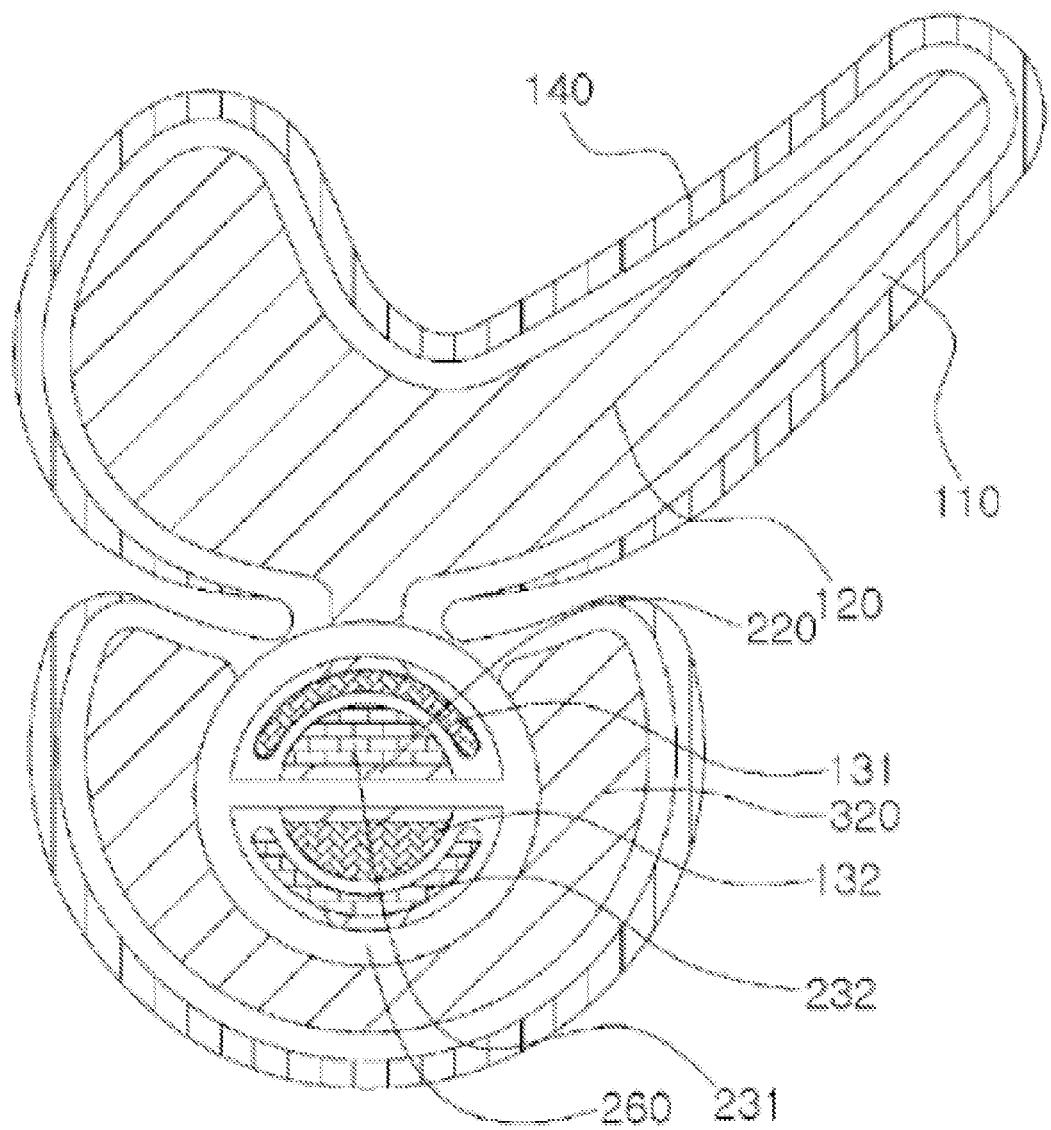
FIG. 15 is a plan view illustrating the patch of FIG. 14 to which a double-sided adhesive film for sealing a battery system is attached.

Next, referring to FIG. 15, the double-sided adhesive film 260 for enclosing both the first and second electrode layers 131 and 231 and the third and fourth electrode layers 132 and 232 is attached on the substrate 110.

Figure 16:
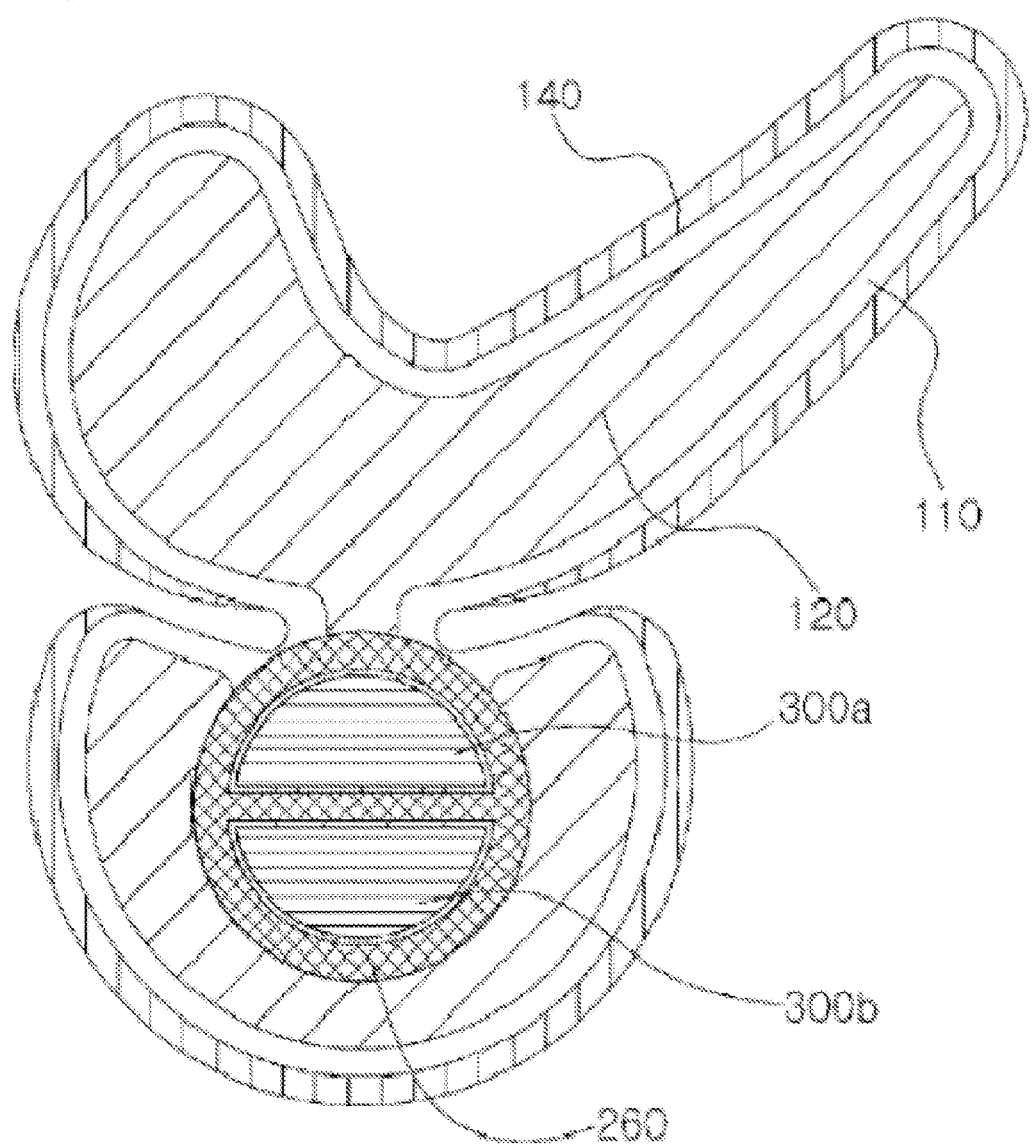
FIG. 16 is a plan view illustrating the patch of FIG. 15 in which an ion conductive electrolyte is coated on each of two unit batteries.
Figure 17:
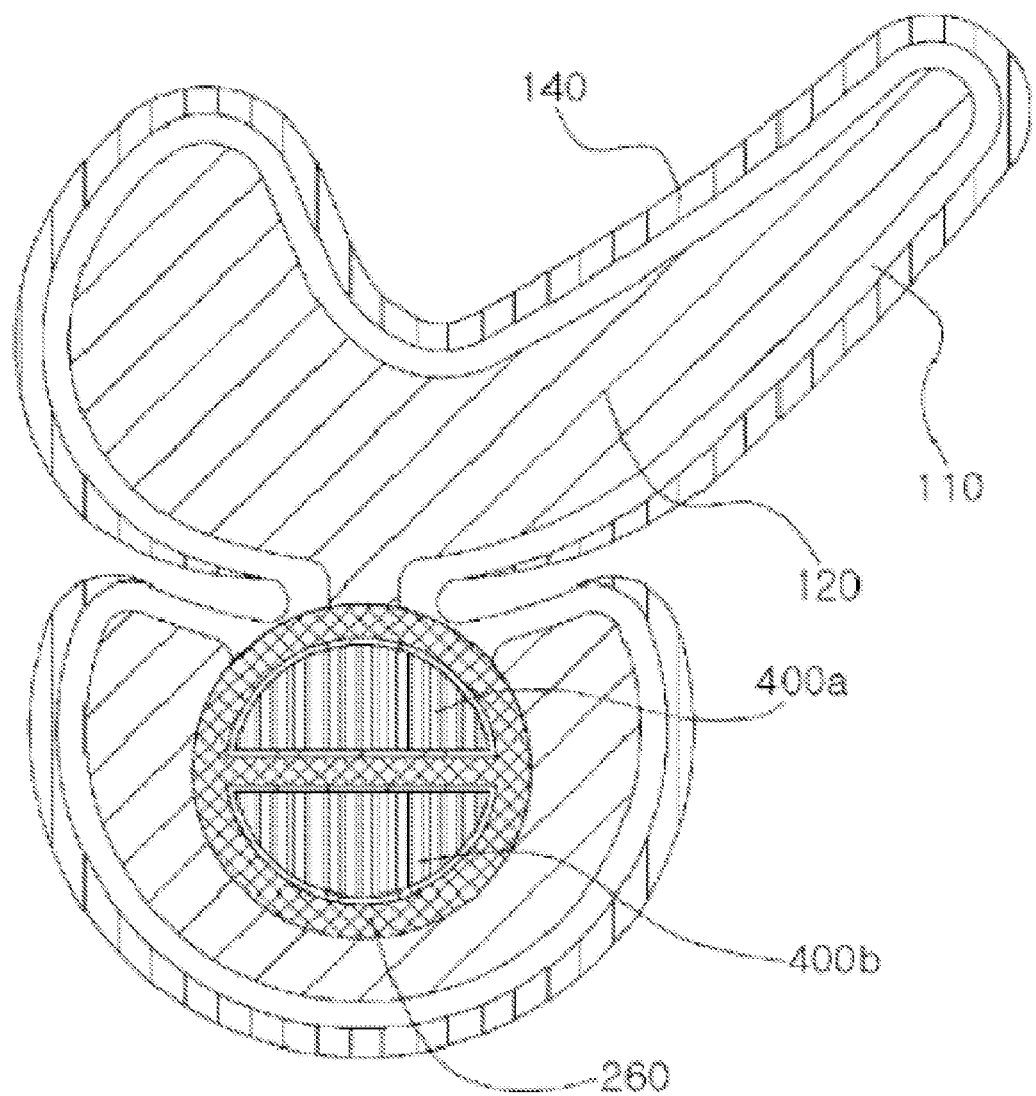
FIG. 17 is a plan view illustrating the patch of FIG. 15 in which a hygroscopic paper impregnated with an ion conductive electrolyte is disposed.

Next, referring to FIG. 16, a first ion conductive polymer electrolyte layer 300a for covering both the first and second electrode layers 131 and 231 and an additional second ion conductive polymer electrolyte layer 300b for covering both the third and fourth electrode layers 132 and 232 are disposed. The two electrolyte layers 300a and 300b are separated by the double-sided adhesive film 260, so that a structure for preventing ions from flowing between the two electrolyte layers 300a and 300b is formed. That is, as illustrated in FIG. 15 or 16, the double-sided adhesive film 260 has two openings, in which the first and second electrode layers 131 and 231 and the first ion conductive polymer electrolyte layer 300a covering the first and second electrode layers 131 and 231 are disposed in one opening, and the third and fourth electrode layers 132 and 232 and the second ion conductive polymer electrolyte layer 300b covering the third and fourth electrode layers 132 and 232 are disposed in the other opening, and the two openings are separated by the double-sided adhesive film 260. Alternatively, as illustrated in FIG. 17, instead of the two ion conductive polymer electrolyte layers 300a and 300b, two hygroscopic papers 400a and 400b impregnated with the ion conductive polymer electrolyte may be used.

The first and second electrode layers 131 and 231 and the ion conductive polymer electrolyte 300a or 400a covering the first and second electrode layers 131 and 231 become the positive electrode, the negative electrode, and the electrolyte disposed therebetween of the one thin film battery, respectively, to form the first unit battery. Further, the third and fourth electrode layers 132 and 232 and the ion conductive polymer electrolyte 300b or 400b covering the third and fourth electrode layers 132 and 232 become the positive electrode, the negative electrode, and the electrolyte disposed therebetween of the other thin film battery, respectively, to form the second unit battery. The two unit batteries are serially connected through the second electrically conductive layer 220 electrically connected with both the second and third electrode layers 231 and 132. The first ion conductive polymer electrolyte layer 300a is separated from the second ion conductive polymer electrolyte layer 300b, so that the flow of ions between the first and second ion conductive polymer electrolyte layers 300a and 300b is prevented. However, both the second electrode layer 231 and the third electrode layer 132 are disposed on the second electrically conductive layer 220 while being in contact with the second electrically conductive layer 220, so that electrons may flow between the second electrode layer 231 and the third electrode layer 132.

Figure 18:
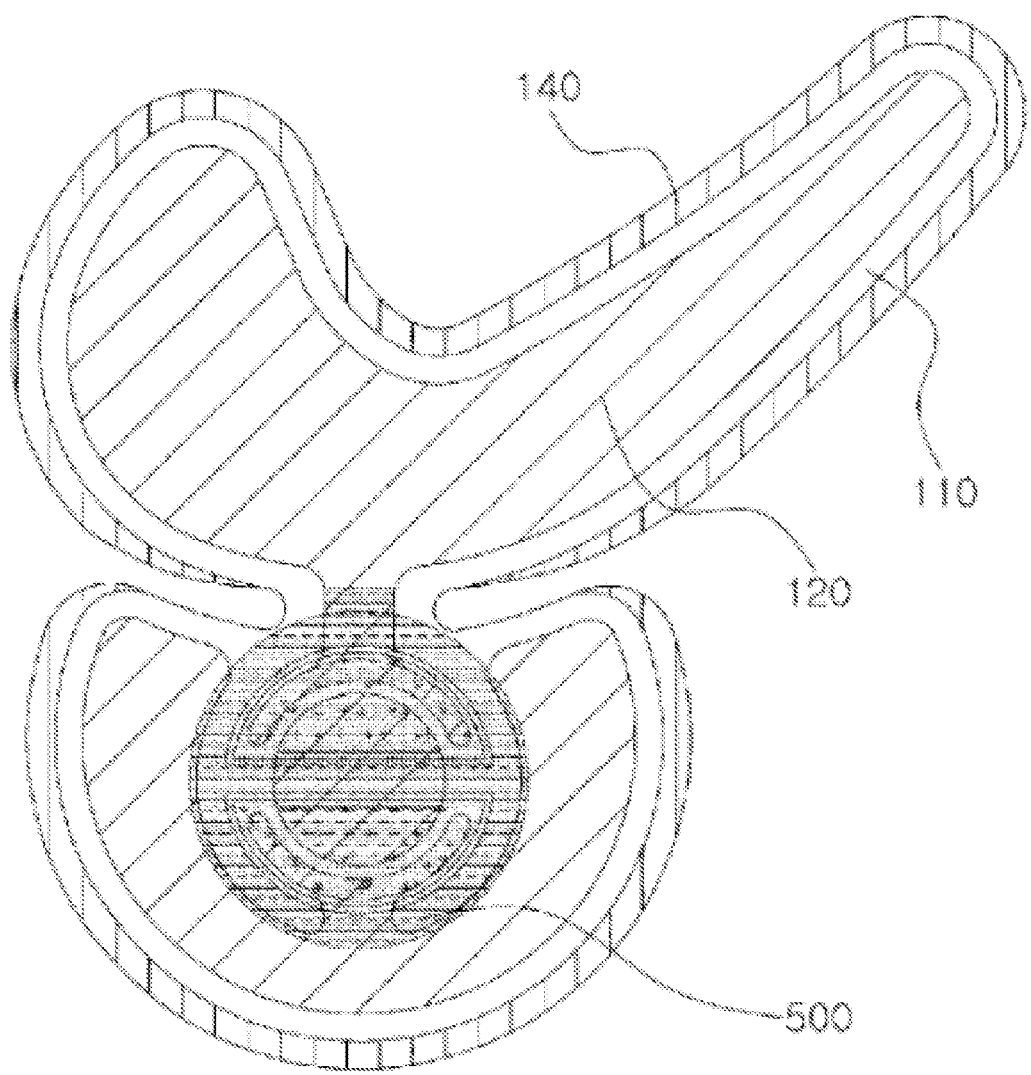
FIG. 18 is a plan view illustrating the patch of FIG. 16 or 17 to which a sealing film for sealing a battery system is attached.

Next, as illustrated in FIG. 18, the two unit batteries are sealed using the sealing film 500, so that the entire battery system is prevented from being exposed to the outside. The sealing film 500 may be disposed while being attached on the double-sided adhesive film 260. In the present embodiment, a material of each member (the substrate, the electrically conductive layers, the electrode layers, the electrolyte, the backing layer, the hygroscopic paper, the double-sided adhesive film, and the sealing film) and a process of manufacturing each member may employ the material and the manufacturing process described in the aforementioned embodiment, so its detailed description will be omitted. As described above, it can be identified that the iontophoresis patch may include the two or more serial-connected unit batteries by simultaneously disposing the plurality of electrode layers within the inside of the iontophoresis patch.

FIGS. 19 to 21 illustrate an apparatus including the thin film battery, especially an RFID tag coupled with the thin film battery according to another embodiment of the present invention. As illustrated in FIG. 19, the first to third electrically conductive layers 120, 220, and 320 are disposed on the substrate 110 of the RFID tag. Next, as illustrated in FIG. 20, the first electrode layer 131 is coated on the first electrically conductive layer 120, the second electrode layer 231 and the third electrode layer 132 are coated on the second electrically conductive layer 220, and the fourth electrode layer 232 is coated on the third electrically conductive layer 330. Next, as illustrated in FIG. 21, the double-sided adhesive film 260 dividing regions of the two unit batteries is coated, the first electrolyte 300a or 400a covering the first and second electrode layers 131 and 231 and the second electrolyte 300b or 400b covering the third and fourth electrode layers 132 and 232 are disposed on the divided regions of the unit batteries, respectively, and then the entire battery system is sealed with the sealing film 500. The first and second electrode layers 131 and 231 and the first electrolyte 300a or 400a covering the first and second electrode layers 131 and 231 form the first unit battery, and the third and fourth electrode layers 132 and 232 and the second electrolyte 300b or 400b covering the third and fourth electrode layers 132 and 232 form the second unit battery. The two unit batteries (the first unit battery and the second unit battery) are serially connected to each other through the second electrically conductive layer 200 likewise to the aforementioned embodiment.

As described above, the present invention may be applied to any small-sized apparatus installed on a substrate having an embedded thin film battery system, as well as an iontophoresis patch. For example, the present invention may be applied to an electronic apparatus, such as a smart card, requiring a small battery or power.

The present invention is not limited by the aforementioned embodiments and the accompanying drawings. The scope of the invention is defined by the accompanying claims, and those skilled in the art will appreciate that various substitutions, modifications, and change are made without departing from the scope and spirit of the invention as disclosed in the accompanying claims.

The invention claimed is:

1. An apparatus, comprising:
a device electrically operating and comprising a substrate; and
a thin film battery for supplying power to the device, wherein the thin film battery comprises:
a first electrically conductive layer formed on the substrate;
a second electrically conductive layer formed on the substrate while being spaced apart from the first electrically conductive layer and positioned on an identical plane to the first electrically conductive layer;
a first electrode layer formed on the first electrically conductive layer and electrically connected to the first electrically conductive layer;
a second electrode layer formed on the second electrically conductive layer, electrically connected to the second electrically conductive layer, while being spaced apart from the first electrode layer, having a polarity opposite to a polarity of the first electrode layer;

an ion conductive polymer electrolyte for covering both the first electrode layer and the second electrode layer;

a sealing film for sealing the ion conductive polymer electrolyte; and wherein the thin film battery comprises two or more serially connected batteries disposed on the substrate, wherein the thin film battery further comprises:

a third electrically conductive layer formed on the substrate while being separated from the first and second electrically conductive layers and positioned on an identical plane to the first electrically conductive layer;

a third electrode layer electrically connected with the second electrically conductive layer on the second electrically conductive layer, while being spaced apart from the second electrode layer, having an identical polarity to the polarity of the first electrode layer;

a fourth electrode layer electrically connected with the third electrically conductive layer on the third electrically conductive layer, while being spaced apart from the third electrode layer, having an identical polarity to the polarity of the second electrode layer; and an additional ion conductive electrolyte separated from the ion conductive polymer electrolyte while covering both the third electrode layer and the fourth electrode layer; and a double-sided adhesive film disposed between the substrate and the sealing film to seal the two or more unit batteries, wherein the double-sided adhesive film has two or more openings, in which the first and second electrode layers and the ion conductive polymer electrolyte covering both the first and second electrode layers are disposed on a first opening and the third and fourth electrode layers and the additional ion conductive electrolyte covering both the third and fourth electrode layers are disposed on a second opening.

2. The apparatus as claimed in claim 1, wherein the first electrode layer and the second electrode layer are disposed on an identical plane.

3. The apparatus as claimed in claim 1, wherein the thin film battery is a closed-type thin film battery, and the substrate and the sealing film have a water blocking property.

4. The apparatus as claimed in claim 3, wherein at least one of the substrate and the sealing film is a polyethylene terephthalate film or a polyacrylonitrile film.

5. The apparatus as claimed in claim 1, wherein the first electrically conductive layer and the second electrically conductive layer contains one or more conductive powder selected from the group consisting of carbon powder, nickel powder, and silver powder.

6. The apparatus as claimed in claim 1, wherein the first electrode layer is a positive electrode layer of the thin film battery, and comprises a binder containing one or more elements selected from the group consisting of polyethylen oxide, polyvinyl pyrrolidone, and polymethyl methacrylate, and manganese dioxide powder.

7. The apparatus as claimed in claim 1, wherein the second electrode layer is a negative electrode layer of the thin film battery, and comprises a binder containing one or more elements selected from the group consisting of polyethylene oxide, polyvinyl pyrrolidone, and polymethyl methacrylate, and zinc powder or zinc alloy powder.

8. The apparatus as claimed in claim 1, wherein the second electrode layer comprises zinc alloy powder to which one or more gas generation inhibiting inhibitors selected from the group consisting of bismuth (Bi), indium (In), and aluminum (Al) are added.

9. The apparatus as claimed in claim 8, wherein at least one of the bismuth (Bi), indium (In), and aluminum (Al) as the inhibitor is contained in the zinc alloy powder by a content of 10 to 1000 ppm, respectively.

10. The apparatus as claimed in claim 1, wherein the ion conductive polymer electrolyte is a gel-type electrolyte to which a polymer material selected from the group consisting of polyethylene oxide, polyvinyl alcohol, and carbonyl methyl cellulose is added.

11. The apparatus as claimed in claim 1, wherein the ion conductive polymer electrolyte is provided while being impregnated in a hygroscopic paper.

12. The apparatus as claimed in claim 1, wherein the sealing film seals the ion conductive polymer electrolyte covering both the first electrode layer and the second electrode layer and the additional ion conductive electrolyte covering both the third electrode layer and the fourth electrode layer.

13. The apparatus as claimed in claim 1, wherein the second electrically conductive layer is disposed between the first electrically conductive layer and the third electrically conductive layer,
the second electrode layer is closely disposed to the first electrode layer so that the first and second electrode layers function as electrodes of a first unit battery, and
the fourth electrode layer is closely disposed to the third electrode layer so that the third and fourth electrode layers function as electrodes of a second unit battery.

14. The apparatus as claimed in claim 1, wherein the first and second electrode layers and the ion conductive polymer electrolyte covering both the first and second electrode layers form a first unit battery,
the third and fourth electrode layers and the additional ion conductive electrolyte covering both the third and fourth electrode layers form a second unit battery, and
the first unit battery and the second unit battery are serially connected to each other through the second electrically conductive layer.

15. The apparatus as claimed in claim 1, wherein the ion conductive polymer electrolyte covering both the first and second electrode layers and the additional ion conductive electrolyte covering both the third and fourth electrode layers are disposed while being separated from each other by the double-sided adhesive film.

16. The apparatus as claimed in claim 1, wherein the device is a Radio Frequency Identification (RFID) tag or a smart card.

* * * * *